US010299851B2

(12) United States Patent
Garrison

(10) Patent No.: US 10,299,851 B2
(45) Date of Patent: *May 28, 2019

(54) DISSECTION SCISSORS ON SURGICAL DEVICE

(71) Applicant: COVIDIEN LP, Mansfield, MA (US)

(72) Inventor: David M. Garrison, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 177 days.

This patent is subject to a terminal disclaimer.

(21) Appl. No.: 15/344,880

(22) Filed: Nov. 7, 2016

(65) Prior Publication Data

US 2017/0049504 A1    Feb. 23, 2017

Related U.S. Application Data

(62) Division of application No. 13/277,962, filed on Oct. 20, 2011, now Pat. No. 9,492,221.

(51) Int. Cl.
*A61B 18/14* (2006.01)
*A61B 18/00* (2006.01)
*A61B 17/29* (2006.01)

(52) U.S. Cl.
CPC ...... *A61B 18/1442* (2013.01); *A61B 18/1445* (2013.01); *A61B 2017/2945* (2013.01);
(Continued)

(58) Field of Classification Search
CPC ............ A61B 18/1442; A61B 18/1445; A61B 2018/146; A61B 2018/00589;
(Continued)

(56) References Cited

U.S. PATENT DOCUMENTS

D249,549 S    9/1978  Pike
D263,020 S    2/1982  Rau, III
(Continued)

FOREIGN PATENT DOCUMENTS

CN    201299462 Y    9/2009
DE    2415263 A1    10/1975
(Continued)

OTHER PUBLICATIONS

U.S. Appl. No. 08/926,869, filed Sep. 10, 1997, James G. Chandler.
(Continued)

*Primary Examiner* — Mark Bockelman

(57) ABSTRACT

A surgical instrument includes an end effector and a housing mechanically coupled to the end effector. The end effector includes a first actuating device configured to perform a first surgical procedure and a second actuating device integrally associated with the first actuating device and configured to perform a second surgical procedure, the second surgical procedure being independently operable and different than the first surgical procedure. An outer portion of the first actuating device and an outer portion of the second actuating device form a portion of an outer housing of the end effector. The housing includes a first actuator, mechanically coupled to the first actuating device and configured to impart movement to the first actuating device and a second actuator, mechanically coupled to the second actuating device and configured to impart movement to the second actuating device.

15 Claims, 12 Drawing Sheets

(52) U.S. Cl.
CPC .......... *A61B 2018/0063* (2013.01); *A61B 2018/00404* (2013.01); *A61B 2018/00428* (2013.01); *A61B 2018/00589* (2013.01); *A61B 2018/00595* (2013.01); *A61B 2018/00601* (2013.01); *A61B 2018/00607* (2013.01); *A61B 2018/00916* (2013.01); *A61B 2018/00922* (2013.01); *A61B 2018/00928* (2013.01); *A61B 2018/00958* (2013.01); *A61B 2018/141* (2013.01); *A61B 2018/146* (2013.01); *A61B 2018/1407* (2013.01); *A61B 2018/1455* (2013.01); *A61B 2018/1457* (2013.01)

(58) Field of Classification Search
CPC ........... A61B 2018/00595; A61B 2018/00607; A61B 2018/1455; A61B 2018/1457; A61B 2017/2945; A61B 2018/1407; A61B 2018/141; A61B 2018/00601; A61B 2018/00916; A61B 2018/00922; A61B 2018/00928; A61B 2018/00958; A61B 2018/00428
See application file for complete search history.

(56) References Cited

U.S. PATENT DOCUMENTS

| | | |
|---|---|---|
| 4,655,216 A | 4/1987 | Tischer |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 4,872,456 A | 10/1989 | Hasson |
| 5,258,006 A | 11/1993 | Rydell et al. |
| D343,453 S | 1/1994 | Noda |
| 5,290,302 A | 3/1994 | Pericic |
| 5,312,434 A | 5/1994 | Crainich |
| 5,320,635 A | 6/1994 | Smith |
| D348,930 S | 7/1994 | Olson |
| D349,341 S | 8/1994 | Lichtman et al. |
| 5,342,381 A | 8/1994 | Tidemand |
| 5,352,222 A | 10/1994 | Rydell |
| 5,356,408 A | 10/1994 | Rydell |
| 5,368,606 A | 11/1994 | Marlow et al. |
| D354,564 S | 1/1995 | Medema |
| D358,887 S | 5/1995 | Feinberg |
| 5,462,546 A | 10/1995 | Rydell |
| 5,514,134 A | 5/1996 | Rydell et al. |
| 5,522,830 A | 6/1996 | Aranyi |
| 5,540,685 A | 7/1996 | Parins et al. |
| 5,569,243 A | 10/1996 | Kortenbach et al. |
| 5,658,281 A | 8/1997 | Heard |
| D384,413 S | 9/1997 | Zlock et al. |
| H1745 H | 4/1998 | Paraschac |
| 5,766,166 A | 6/1998 | Hooven |
| 5,776,146 A | 7/1998 | Sackier et al. |
| 5,827,281 A | 10/1998 | Levin |
| D402,028 S | 12/1998 | Grimm et al. |
| D408,018 S | 4/1999 | McNaughton |
| 5,908,420 A | 6/1999 | Parins et al. |
| D416,089 S | 11/1999 | Barton et al. |
| D424,694 S | 5/2000 | Tetzlaff et al. |
| D425,201 S | 5/2000 | Tetzlaff et al. |
| RE36,795 E | 7/2000 | Rydell |
| H1904 H | 10/2000 | Yates et al. |
| 6,174,309 B1 | 1/2001 | Wrublewski et al. |
| D449,886 S | 10/2001 | Tetzlaff et al. |
| D453,923 S | 2/2002 | Olson |
| D454,951 S | 3/2002 | Bon |
| 6,358,268 B1 | 3/2002 | Hunt et al. |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| 6,506,208 B2 | 1/2003 | Hunt et al. |
| 6,527,785 B2 | 3/2003 | Sancoff et al. |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,931,649 B2 | 4/2011 | Couture et al. |
| 7,955,332 B2 | 6/2011 | Arts et al. |
| 8,012,166 B2 | 9/2011 | Rizvi |
| D649,249 S | 11/2011 | Guerra |
| D649,643 S | 11/2011 | Allen, IV et al. |
| 9,492,221 B2 | 11/2016 | Garrison |
| 2002/0072766 A1 | 6/2002 | Hunt et al. |
| 2009/0209946 A1 | 8/2009 | Swayze et al. |
| 2009/0234355 A1 | 9/2009 | Edwards et al. |
| 2011/0004210 A1 | 1/2011 | Johnson et al. |
| 2012/0059371 A1 | 3/2012 | Anderson et al. |
| 2012/0078250 A1 | 3/2012 | Orton et al. |
| 2012/0083785 A1 | 4/2012 | Roy et al. |
| 2012/0083786 A1 | 4/2012 | Artale et al. |
| 2012/0083827 A1 | 4/2012 | Artale et al. |
| 2012/0095456 A1 | 4/2012 | Schechter et al. |
| 2012/0095460 A1 | 4/2012 | Rooks et al. |

FOREIGN PATENT DOCUMENTS

| | | |
|---|---|---|
| DE | 2514501 A1 | 10/1976 |
| DE | 2627679 A1 | 1/1977 |
| DE | 3423356 A1 | 1/1986 |
| DE | 3612646 A1 | 4/1987 |
| DE | 8712328 U1 | 2/1988 |
| DE | 4303882 A1 | 8/1994 |
| DE | 4403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19738457 A1 | 3/1999 |
| DE | 19751108 A1 | 5/1999 |
| DE | 19946527 C1 | 7/2001 |
| DE | 10045375 A1 | 4/2002 |
| DE | 102004026179 A1 | 12/2005 |
| DE | 202007009165 U1 | 8/2007 |
| DE | 202007009317 U1 | 8/2007 |
| DE | 202007016233 U1 | 1/2008 |
| DE | 102008018406 B3 | 7/2009 |
| EP | 1159926 A2 | 12/2001 |
| JP | 61501068 | 9/1984 |
| JP | 6502328 | 3/1992 |
| JP | 55106 | 1/1993 |
| JP | 540112 | 2/1993 |

(56) References Cited

FOREIGN PATENT DOCUMENTS

| | | |
|---|---|---|
| JP | 6121797 | 5/1994 |
| JP | 6285078 | 10/1994 |
| JP | 6343644 | 12/1994 |
| JP | 6511401 | 12/1994 |
| JP | 7265328 | 10/1995 |
| JP | 856955 | 3/1996 |
| JP | 8317936 | 3/1996 |
| JP | 8289895 | 5/1996 |
| JP | 8252263 | 10/1996 |
| JP | 8317934 | 12/1996 |
| JP | 910223 | 1/1997 |
| JP | 9122138 | 5/1997 |
| JP | 1024051 | 1/1998 |
| JP | 11070124 | 5/1998 |
| JP | 10155798 | 6/1998 |
| JP | 1147150 | 2/1999 |
| JP | 11169381 | 6/1999 |
| JP | 11192238 | 7/1999 |
| JP | 11244298 | 9/1999 |
| JP | 2000102545 A | 4/2000 |
| JP | 2000342599 A | 12/2000 |
| JP | 2000350732 A | 12/2000 |
| JP | 20018944 | 1/2001 |
| JP | 200129356 | 2/2001 |
| JP | 2001128990 A | 5/2001 |
| JP | 2001190564 A | 7/2001 |
| JP | 20013400 | 11/2001 |
| JP | 2002528166 A | 9/2002 |
| JP | 2003245285 A | 9/2003 |
| JP | 2004517668 A | 6/2004 |
| JP | 2004528869 A | 9/2004 |
| JP | 2011125195 A | 6/2011 |
| JP | 6030945 B2 | 11/2016 |
| SU | 401367 A1 | 10/1973 |
| WO | WO-0036986 A1 | 6/2000 |
| WO | WO-0059392 A1 | 10/2000 |
| WO | WO-0115614 A1 | 3/2001 |
| WO | WO-0154604 A1 | 8/2001 |
| WO | WO-05110264 A3 | 4/2006 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremcich.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/028,810, filed Feb. 16, 2011, Robert M. Sharp.
U.S. Appl. No. 13/030,231, filed Feb. 18, 2011, Jeffrey M. Roy.
U.S. Appl. No. 13/050,182, filed Mar. 17, 2011, Glenn A. Homer.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.
U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Homer.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/344,729, filed Jan. 6, 2012, James D. Allen, IV.
U.S. Appl. No. 13/355,829, filed Jan. 23, 2012, John R. Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/358,657, filed Jan. 26, 2012, Kim V. Brandt.
U.S. Appl. No. 13/360,925, filed Jan. 30, 2012, James H. Orszulak.
U.S. Appl. No. 13/369,152, filed Feb. 8, 2012, William H. Nau, Jr.
U.S. Appl. No. 13/400,290, field Feb. 20, 2012, Eric R. Larson.
U.S. Appl. No. 13/401,964, filed Feb. 22, 2012, John R. Twomey.
U.S. Appl. No. 13/404,435, filed Feb. 24, 2012, Kim V. Brandt.
U.S. Appl. No. 13/404,476, filed Feb. 24, 2012, Kim V. Brandt.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC; Date: Aug. 2003.

(56) References Cited

OTHER PUBLICATIONS

Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.

(56) References Cited

OTHER PUBLICATIONS

Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.
Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

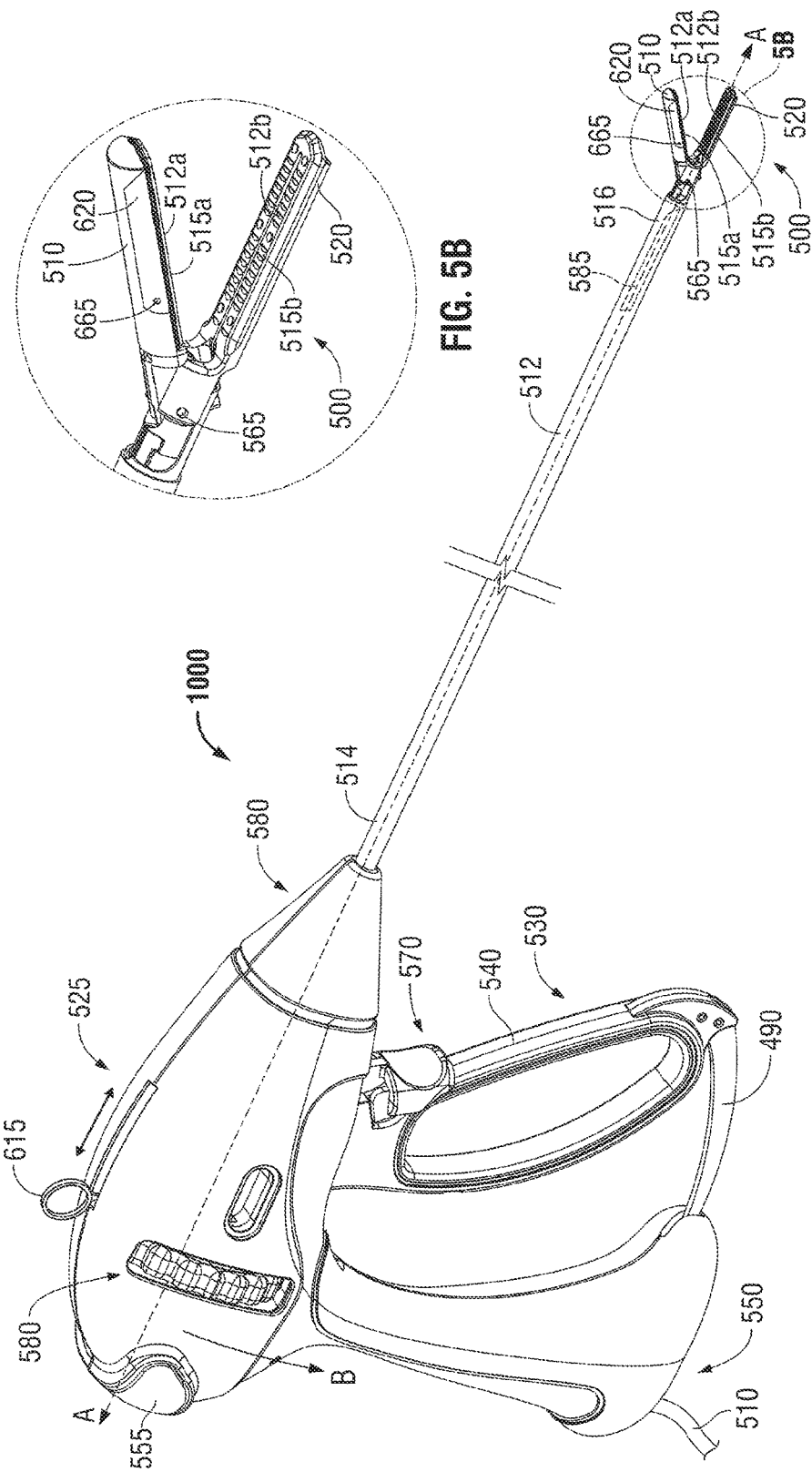

DISSECTION SCISSORS ON SURGICAL DEVICE

CROSS-REFERENCE TO RELATED APPLICATION

This application is a divisional application claiming the benefit of and priority to U.S. patent application Ser. No. 13/277,962, filed on Oct. 20, 2011, the entire contents of which is hereby incorporated by reference herein.

BACKGROUND

Technical Field

The present disclosure relates to a multi-functional surgical device for use with open or endoscopic surgical procedures including a multi-functional end effector. More particularly, the present disclosure relates to an electrosurgical device with a cutting device formed in the multi-functional end effector.

Description of Related Art

A variety of electrosurgical devices are commonly used in open and endoscopic surgical procedures. One device commonly used in both open and endoscopic procedures is a hemostat or forceps. A hemostat or forceps is a simple plier-like tool which uses mechanical action between its jaws to constrict vessels and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize and/or seal tissue.

By utilizing an electrosurgical forceps, a surgeon can either cauterize, coagulate/desiccate, reduce or slow bleeding and/or seal vessels by controlling the intensity, frequency and duration of the electrosurgical energy applied to the tissue. Generally, the electrical configuration of electrosurgical forceps can be categorized in two classifications: 1) monopolar electrosurgical forceps; and 2) bipolar electrosurgical forceps.

Monopolar forceps utilize one active electrode associated with the clamping multi-functional end effector and a remote patient return electrode or pad which is typically attached externally to the patient. When the electrosurgical energy is applied, the energy travels from the active electrode, to the surgical site, through the patient and to the return electrode.

Bipolar electrosurgical forceps utilize two generally opposing electrodes that are disposed on the inner opposing surfaces of the multi-functional end effectors and which are both electrically coupled to an electrosurgical generator. Each electrode is charged to a different electric potential. Since tissue is a conductor of electrical energy, when the effectors are utilized to grasp tissue therebetween, the electrical energy can be selectively transferred through the tissue.

In order to effect a proper seal with larger vessels or thick tissue, two predominant mechanical parameters must be accurately controlled: the pressure applied to the tissue; and the gap distance between the electrodes. As can be appreciated, both of these parameters are affected by the thickness of vessels or tissue. More particularly, accurate application of pressure is important for several reasons: to reduce the tissue impedance to a low enough value that allows enough electrosurgical energy through the tissue; to overcome the forces of expansion during tissue heating; and to contribute to the end tissue thickness which is an indication of a good seal. It has been determined that fused tissue is optimum between about 0.001 inches to about 0.006 inches for small vessels and tissues and about 0.004 inches to about 0.008 inches for large, soft tissue structures. Below these ranges, the seal may shred or tear and above this range the tissue may not be properly or effectively sealed.

With respect to smaller vessels, the pressure applied to the tissue tends to become less relevant whereas the gap distance between the electrically conductive surfaces becomes more significant for effective sealing. In other words, the chances of the two electrically conductive surfaces touching during activation increases as the vessels become smaller.

Electrosurgical methods may be able to seal larger vessels using an appropriate electrosurgical power curve, coupled with an instrument capable of applying a large closure force to the vessel walls. It is thought that the process of coagulating small vessels is fundamentally different than electrosurgical vessel sealing. For the purposes herein, "coagulation" is defined as a process of desiccating tissue wherein the tissue cells are ruptured and dried and vessel sealing is defined as the process of liquefying the collagen in the tissue so that it reforms into a fused mass. Thus, coagulation of small vessels is sufficient to permanently close them. Larger vessels need to be sealed to assure permanent closure.

The present disclosure provides a multi-functional surgical arrangement that may be incorporated into an open surgical device, an endoscopic surgical device or any other suitable surgical instrument. The multi-functional surgical arrangement includes a first device and second device, wherein the first device provides the primary function of the device and a second device provides one or more secondary functions of the device, such as, a cutting feature. The first device and the second device, in addition to providing primary and secondary functions, may together provide additional functionality separate from the primary and secondary functions provided by the first and second devices.

SUMMARY

As used herein, the term "distal" refers to that portion that is further from an operator while the term "proximal" refers to that portion that is closer to an operator. As used herein, the term "treat" refers to performing a surgical treatment to tissue using energy, e.g. heating, sealing, or energized cutting of tissue. As used herein, the terms "energy" and "electrosurgical energy" refers broadly to include all types of energy used to treat tissue, e.g., RF energy, ultrasonic energy, microwave energy, thermal energy, light energy, etc. As used herein, the term "vessel sealing" is defined as the process of liquefying the collagen, elastin and ground substances in the tissue so that the tissue reforms into a fused mass with significantly-reduced demarcation between the opposing tissue structures. The process of "vessel sealing" may be performed on any tissue type.

According to an aspect of the present disclosure, a bipolar electrosurgical instrument includes a housing mechanically coupled to an end effector. The end effector includes a first actuating device configured to perform a first surgical procedure and a second actuating device, integrally associated with the first actuating device and configured to perform a second surgical procedure. The second surgical procedure is independently operable and different than the first surgical procedure. The outer portion of the first actuating device and an outer portion of the second actuating device form a portion of an outer housing of the end effector. The housing includes a first actuator and a second actuator. The first actuator is mechanically coupled to the first actuating device and configured to impart movement thereto. The second actuator is mechanically coupled to the second actuating device and configured to impart movement to the second actuating device.

The first actuating device may further include a first jaw member and a second jaw member that move relative to one another about a first pivot. The first and second jaw members move from a first position, wherein the first and second jaw member are disposed in spaced relation relative to one another, to a second position, wherein the first and second jaw member cooperate to perform the first surgical procedure on tissue positioned therebetween. The first actuator actuates the first jaw member and/or the second jaw member about the first pivot.

The second actuating device may further include a cutting device integrally associated with the first jaw member and configured to move relative to the first jaw member about a second pivot, the second pivot being independent of the first pivot. The cutting device may move from a first position, wherein the first jaw member and at least a portion of the cutting device are disposed in a spaced relationship relative to one another, to a second position, wherein the cutting device forms part of the first jaw member. The first jaw member and cutting device cooperate to perform the second surgical procedure on tissue positioned therebetween. The second actuator actuates the cutting device and/or the first jaw member about the second pivot.

In a further aspect, the first surgical procedure is tissue sealing and the second surgical procedure is tissue cutting. The first and second jaw members are adapted to connect to a source of electrosurgical energy and are capable of selectively conducting energy through tissue held therebetween to effect a tissue seal. The cutting device and first jaw member are configured to cut tissue positioned therebetween. The cutting device includes a first shearing surface and the first jaw member includes a second shearing surface, wherein the first shearing surface and second shearing surface cooperate to cut tissue therebetween in a scissor-like fashion. In a further aspect, the cutting device formed by the first and second shearing surfaces is substantially curved.

The cutting device may include one or more electrodes configured to selectively connect to a source of electrosurgical energy and the cutting device electrosurgically cuts tissue positioned between the cutting device and the first jaw member in a monopolar fashion.

The first jaw member may include first and second electrosurgical conductive surfaces and may selectively conduct electrosurgically energy between the first electrosurgical conductive surface and the second jaw member and between the second electrosurgical conductive surface and the cutting device in a bipolar fashion.

According to another aspect of the present disclosure, a surgical instrument includes a housing mechanically coupled to an end effector. The end effector includes first and second actuating devices. The first actuating device includes first and second treatment members that moves relative to one another about a first pivot and are adapted to selectively connect to a source of electrosurgical energy. The first actuation device is configured to seal tissue positioned between the first treatment member and the second treatment member. The second actuating device is integrally associated with the first actuating member and includes a third treatment member. The third treatment member moves relative to the first treatment member about a second pivot, the second pivot being different than the first pivot. The third treatment member selectively connects to a source of electrosurgical energy and is configured to cut tissue positioned between the first treatment member and the third treatment member. The outer portion of the first actuating device and an outer portion of the second actuating device form a portion of an outer housing of the end effector. The housing including a first actuator, a second actuator and a switch. The first actuator is mechanically coupled to the first actuating device and configured to impart movement thereto. The second actuator is mechanically coupled to the second actuating device and configured to impart movement to the second actuating device. The switch is configured to select the mode of operation for the surgical instrument.

The switch may be configured to select a bipolar sealing mode wherein the first treatment member receive electrosurgical energy at a first potential and the second treatment member receive electrosurgical energy at a second potential different than the first potential. The first actuating device provides treatment to the tissue positioned between the first treatment member and the second treatment member to seal tissue in a bipolar fashion.

The switch may be configured to select a bipolar cutting mode wherein the first and second treatment members receive electrosurgical energy at a first potential, the third treatment member receives electrosurgical energy at a second potential different than the first potential and the second actuating device provides treatment to tissue positioned between the first treatment member and the second treatment member to cut tissue in a bipolar fashion.

The switch may be configured to select a monopolar sealing mode wherein at least one of the first treatment member and the second treatment member receive electrosurgical energy at a first potential and electrically cooperate with a remotely disposed return pad engaged to patient tissue. The first actuating device provides treatment to tissue positioned between the first and second treatment members to seal tissue in a monopolar fashion.

The switch may be configured to select a monopolar cutting mode wherein the third treatment member receives electro surgical energy at a first potential and electrically cooperates with a remotely disposed return pad engaged to patient tissue. The second actuating device provides treatment to tissue positioned between the first treatment member and the third treatment member to cut tissue in a monopolar fashion.

The switch may be configured to select between bipolar sealing between the first and second treatment members, monopolar sealing between at least one of the first and second treatment members and a remotely disposed return pad engaged to patient tissue, bipolar cutting between the third treatment member and the first and second treatment members, and monopolar cutting between the third treatment member and the remotely disposed return pad engaged to patient tissue.

BRIEF DESCRIPTION OF THE DRAWINGS

Various aspects of the subject instrument are described herein with reference to the drawings wherein:

FIG. 5A is a right, perspective view of a forceps for use in an endoscopic surgical procedure with a multi-functional end effector according to another aspect of the present disclosure;

FIG. 5B is a enlarged, perspective view of the end effector of the forceps in FIG. 5A;

DETAILED DESCRIPTION

The present disclosure relates to a multi-functional electro-mechanical surgical device for use with open or endoscopic surgical procedures including a multi-functional end effector. Although the figure drawings depict a forceps 10, 1000 forming a multi-functional electro-mechanical surgical device for use in connection with tissue and vessel sealing in open and endoscopic surgical procedures, the present disclosure, systems and methods described herein may be used for any electrosurgical instruments, such as, for example, an ablation device, an electrosurgical coagulation device, an electrosurgical cauterization device and/or a electrosurgical resection device. These other types of electrosurgical surgical instruments may be configured to incorporate one or more aspects of the present disclosure.

For the purposes herein, the open forceps 10 and endoscopic forceps 1000 are described in terms of operation and function and further described in terms including a multi-functional end effector assembly 100, 500, respectively. It is contemplated that the aspects of the multi-functional end effector of the forceps 10, 1000, as described hereinbelow, may be applied to any surgical device utilizing the same or similar operating components and features as described below.

Multi-Function Open Surgical Device

Figure 1:
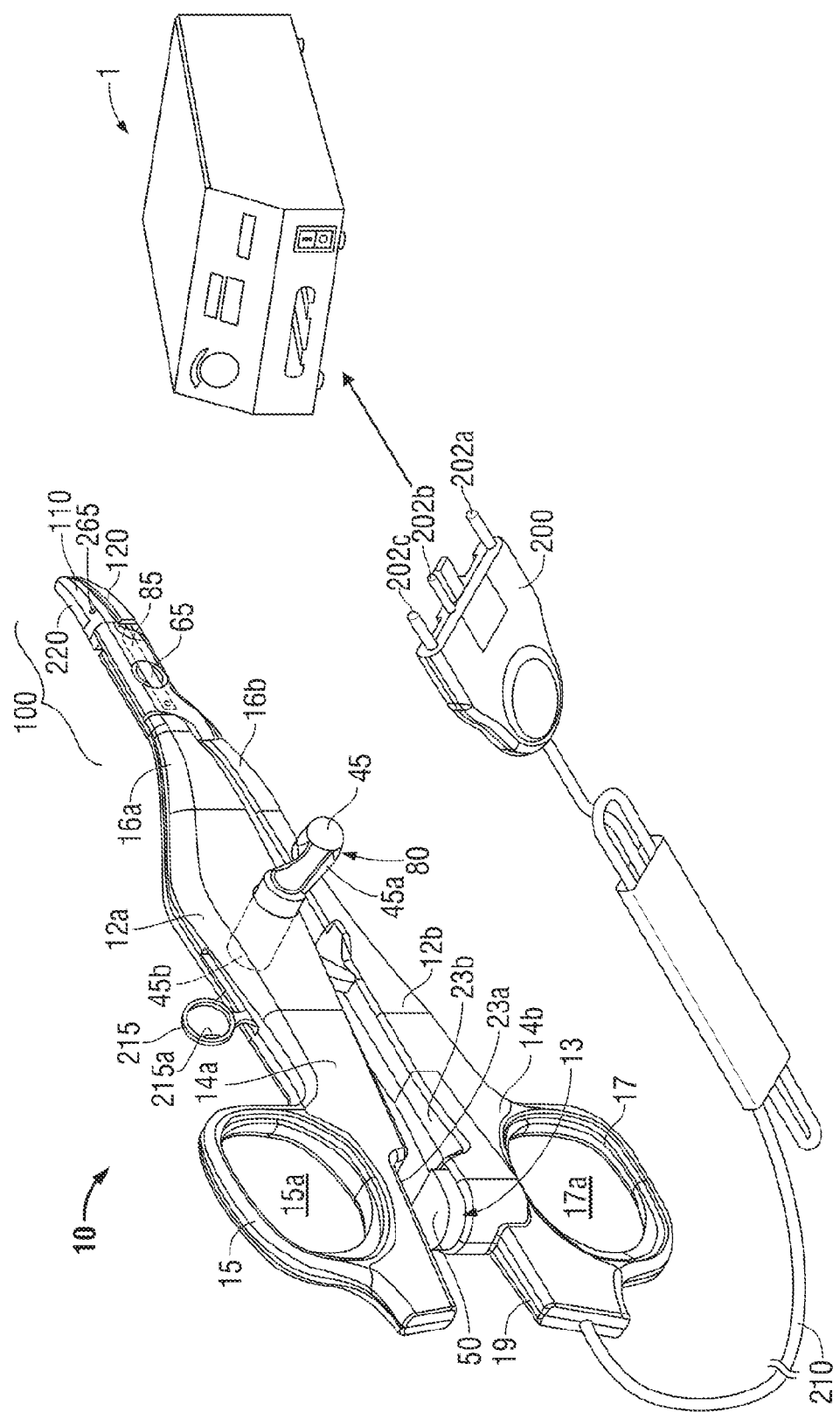
FIG. 1 is a right, perspective view of a forceps for use in an open surgical procedure with a multi-functional end effector according to one aspect of the present disclosure.

Referring initially to FIGS. 1 and 2, a forceps 10 (hereinafter "forceps 10") for use with open surgical procedures includes a pair of opposable shafts 12a, 12b having a multi-functional end effector assembly 100 on the distal ends thereof. In the drawings and in the description that follows, the term "proximal", as is traditional, will refer to the end of the forceps 10 that is closer to the user, while the term "distal" will refer to the end that is further from the user.

Each shaft 12a and 12b includes a handle 15 and 17, respectively, disposed at a proximal end 14a and 14b thereof that defines a finger hole 15a and 17a, respectively, therethrough for receiving a finger of the user. Handles 15 and 17 facilitate movement of the shafts 12a and 12b relative to one another which, in turn, pivot the jaw members 110 and 120 from an open condition wherein the jaw members 110 and 120 are disposed in spaced relation relative to one another to a clamping or closed condition wherein the jaw members 110 and 120 cooperate to grasp tissue therebetween.

Figure 2A:
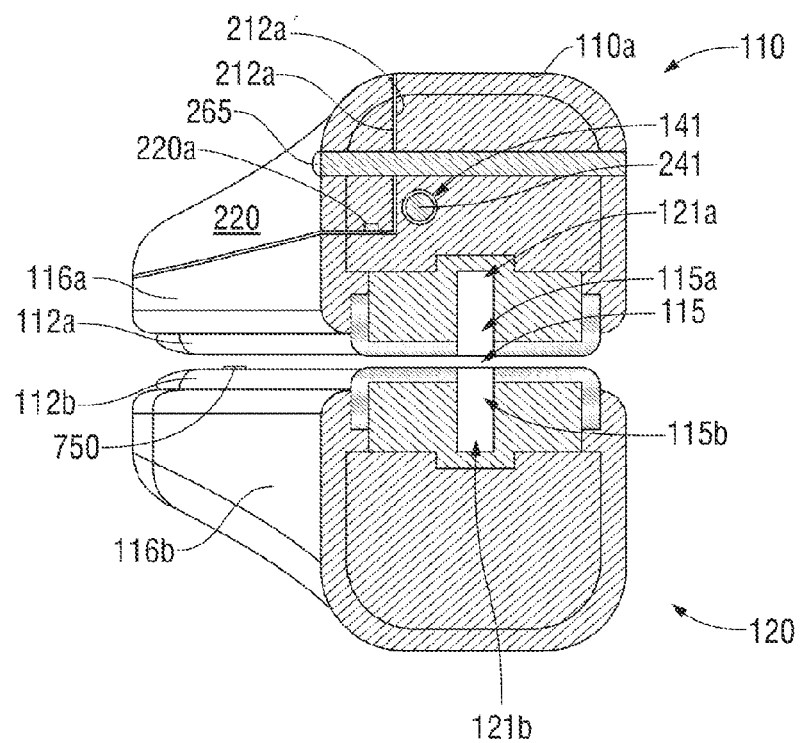
FIG. 2A is a rear, perspective view in partial cross-section of the multi-functional end effector assembly of the forceps of FIG. 1 in a closed condition.
Figure 2B:
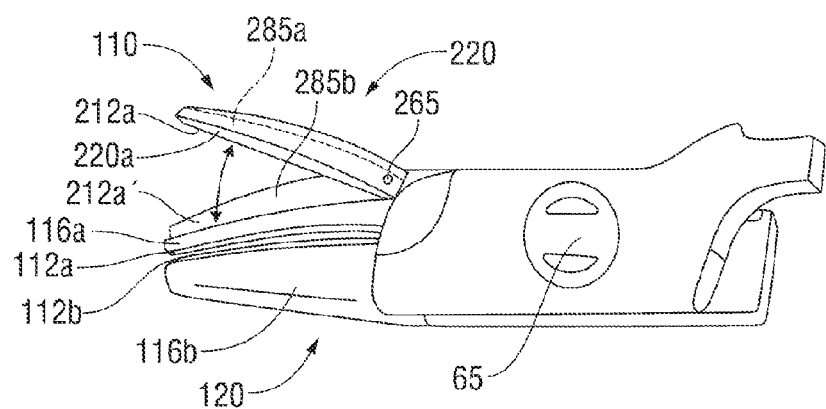
FIG. 2B is a rear, perspective view of the multi-functional end effector assembly of the forceps of FIG. 1 in an open condition.

The arrangement of shaft 12b is slightly different from shaft 12a. More particularly, shaft 12a is generally hollow to house a knife 85 and a knife actuating mechanism 80 operatively associated with a trigger 45. Trigger 45 includes handle members 45a and 45b disposed on opposing sides of shaft 12a to facilitate left-handed and right-handed operation of trigger 45. Trigger 45 is operatively associated with the knife actuating mechanism 80 that includes a series of suitable inter-cooperating elements configured to mechanically cooperate to actuate the knife 85 through tissue grasped between jaw members 110 and 120 upon actuation of trigger 45. Handle members 45a and 45b operate in identical fashion such that use of either of handle members 45a and 45b operates the trigger 45 to reciprocate the knife 85 through the knife channel 115 (FIGS. 2A, 2B). The proximal end 14b of shaft 12b includes a switch cavity 13 protruding from an inner facing surface 23b of shaft 12b configured to seat a depressible switch 50 therein (and the electrical components associated therewith). Switch 50 aligns with an opposing inner facing surface 23a of the proximal end 14a of shaft 12a such that upon approximation of shafts 12a and 12b toward one another, the switch 50 is depressed into biasing engagement with the opposing inner facing surface 23a of the proximal end 14a of shaft 12a.

An electrosurgical cable 210 having a plug 200 at a proximal end thereof connects the forceps 10 to an electrosurgical generator 1. More specifically, the distal end of the electrosurgical cable 210 is securely held to the shaft 12b by a proximal shaft connector 19 and the proximal end of the electrosurgical cable 210 includes a plug 200 having prongs 202a, 202b, and 202c that are configured to electrically and mechanically engage the electrosurgical generator 1. The interior of electrosurgical cable 210 houses a plurality of conductor leads (not explicitly shown) that extend from the prongs 202a, 202b, 202c in the plug 200, through the electrosurgical cable 210 and shaft 12b to provide electrosurgical energy to the distal end of the forceps 10. The delivery of electrosurgical energy is controlled by one or more control switches housed in the forceps 10. The number of prongs in the plug 200 and conductors leads 202a-202c are related and correspond to the number of electrodes in the multi-functional end effector configured to deliver electrosurgical energy and may include any number of prongs and conductor leads.

The forceps 10 includes a multi-functional end effector assembly 100 that attaches to the distal ends 16a and 16b of shafts 12a and 12b, respectively. The multi-functional end effector assembly 100 includes a first actuating device and a second actuating device, wherein the first actuating device provides the primary function of the multi-functional forceps and the second actuating device provides the secondary function of the multifunctional end effector assembly 100. In this particular aspect, the first actuating device includes a pair of opposing jaw members (e.g., upper jaw member 110 and lower jaw member 120) that are pivotably connected and movable relative to one another about a first pivot 65 to grasp, seal and/or cut tissue positioned therebetween. The second actuating device includes the upper jaw member 110 and a shear blade 220 that pivotably connects thereto and is movable relative to jaw member 110 about a second pivot 265 disposed in jaw member 110 to cut and/or shear tissue. The second actuating device may, grasp, spread, cut and/or shear tissue by mechanical cutting, electrical cutting or electro-mechanical cutting tissue, may grasp tissue by the actuation of the shear blade 220 and may spread tissue by opening the shear blade 220 to an open condition. The first actuating device and second actuating device may operate independent of each other or may operate in cooperation with each other.

As best shown in FIG. 2A, electrically conductive sealing surfaces 112a, 112b of upper and lower jaw member 110 and 120, respectively, are pronounced from the respective jaw housings 116a, 116b such that tissue is grasped by the opposing electrically conductive sealing surfaces 112a and 112b when jaw members 110 and 120 are in the closed condition. At least one of the jaw members, e.g., jaw member 120, includes one or more stop members 750 disposed on the inner facing surfaces of the electrically conductive sealing surface 112b. Alternatively or in addition, the stop member(s) 750 may be disposed adjacent to the electrically conductive sealing surfaces 112a, 112b or proximate the first pivot 65. The stop member(s) 750 facilitate gripping and manipulation of tissue and define a gap between opposing jaw members 110 and 120 during sealing and cutting of tissue. In some aspects, the stop member(s) 750 maintain a gap distance between opposing jaw members 110 and 120 within a range of about 0.001 inches (~0.03 millimeters) to about 0.006 inches (~0.015 millimeters). By controlling the intensity, frequency, and duration of the electrosurgical energy applied to the tissue, the user can seal tissue. In some aspects, the gap distance between opposing sealing surfaces 112a and 112b during sealing ranges from about 0.001 inches to about 0.006 inches.

One (or both) of the jaw members (e.g., jaw member 110) may include a knife channel 115a defined therein and configured to facilitate reciprocation of a knife 85 (See FIG. 1) therethrough. Jaw member 120 may also or alternatively include a knife channel 115b defined therein that cooperates with knife channel 115a to reciprocate the knife 85. In this instance, knife channels 115a, 115b define a common knife channel 115.

In this particular aspect, a complete knife channel 115 is formed by the two opposing knife channel halves 115a and 115b associated with respective jaw members 110 and 120. The tissue grasping portions of the jaw members 110 and 120 are generally symmetrical and include similar components and features that cooperate to permit rotation of the jaw members 110, 120 about first pivot 65 to effect the grasping and sealing of tissue. In some aspects, the width of knife channels 115a and 115b and their respective troughs 121a and 121b may be equal along an entire length thereof.

Lower jaw member 120 is generally symmetrical with the upper jaw member 110. Lower jaw member 120 mates with upper jaw member 110 thereby allowing forceps 10 to grasp, seal and/or cut tissue. In use, a user applies closure pressure on shafts 12a and 12b to depress switch 50. A first threshold is met corresponding to the closure force applied to switch 50 as a function of displacement of switch 50 that causes switch 50 to generate a first tactile response that corresponds to a complete grasping of tissue disposed between jaw members 110 and 120. Following the first tactile response, as the user applies additional closure pressure on shafts 12a and 12b, a second threshold is met corresponding the closure force applied to switch 50 as a function of displacement of switch 50 that causes the switch 50 to generate a second tactile response that corresponds to a signal being generated to the electrosurgical generator 1 to supply electrosurgical energy to the sealing surfaces 112a and 112b.

As illustrated in FIGS. 1, 2A and 2B, shear blade actuator 215 (See FIG. 1) is configured to actuate the shear blade 220 between a closed condition, as illustrated in FIGS. 1 and 2A, and an open condition, as illustrated in FIG. 2B. Positioning the shear blade actuator 215 in a most proximal position closes the shear blade 220 and positioning the shear blade actuator 215 in a most distal position opens the shear blade 220. Sliding the shear blade actuator 215 proximally from a most distal position manipulates an actuation rod 241 (See also actuation rod 441a-441d in FIGS. 4A-4D) disposed in a rod channel 141 defined in jaw member 110 to actuate the shear blade 220 between an open condition, as illustrated in FIG. 2B, and a closed condition, as illustrated in FIGS. 1 and 2A.

The shear blade 220 pivots about the second pivot 265 exposing a shear surface 212a and a fixed shear surface 212a' on jaw member 110 that cooperate to cut tissue. The shearing/cutting action between the cutting edge of the shear surface 212a and the shear surface 212a' may be mechanical, electrical and/or electro-mechanical or the forceps 10 may be configured for a clinician to select between mechanical cutting, electrical cutting or any electro-mechanical combination thereof.

Shear surfaces 212a, 212a' may be formed from any suitable material, such as, for example, metal, ceramic or plastic. The shear surfaces 212a, 212a' may include any suitable cutting surface, such as, for example, a straight and/or smooth finished surface, a beveled edge, a sharpened edge or a serrated finished surface. Shear surfaces 212a, 212a' may include a bend (e.g., slight curvature toward each other) and/or a turn (e.g., rotational curvature) to facilitate cutting.

With mechanical shearing/cutting, the shear surface 212a and the fixed shear surface 212a' may be formed and fitted such that the two surfaces remain in contact while the shear blade actuator 215 actuates the shear blade 220 between an open condition and a closed condition.

With electrosurgical or electromechanical cutting, one or more electrodes may be disposed on the shear blade 220 and/or the upper jaw member 110 and the electrodes may be arranged and/or configured to delivery electrosurgical energy in a monopolar or bipolar manner. For example, a portion of the shear surface 212a may form one electrode 285a and the shear surface 212a' may include an opposing electrode 285b that cooperates to treat tissue. The electrodes 285a, 285b may be configured to deliver electrosurgical energy while closing the shear blade 220. In a monopolar cutting mode, the electrosurgical energy delivered to tissue by electrodes 285a, 285b is the same potential and is returned to the electrosurgical generator through a grounding electrode positioned on the patient (not shown). In a bipolar cutting mode, the electrosurgical energy is passed between the electrodes 285a, 285b.

Electrosurgical energy may be delivered in a non-contact CUT mode wherein the electrosurgical energy creates a wedge between the electrodes 285a, 285b and the target tissue. In this configuration of energy delivery the shear blade 220 and the jaw member 110 are disposed in the while articulating from an open condition and the surgeon moves the electrical wedge through tissue in a forward motion.

Cutting may also utilize electro-mechanical cutting wherein electrical and mechanical cutting cuts tissue and electrosurgical energy is further provided to coagulate the cut tissue. In one aspect, bipolar electrosurgical energy is passed between the electrodes 285a and 285b during closing of the shear blade 220.

Figure 3:
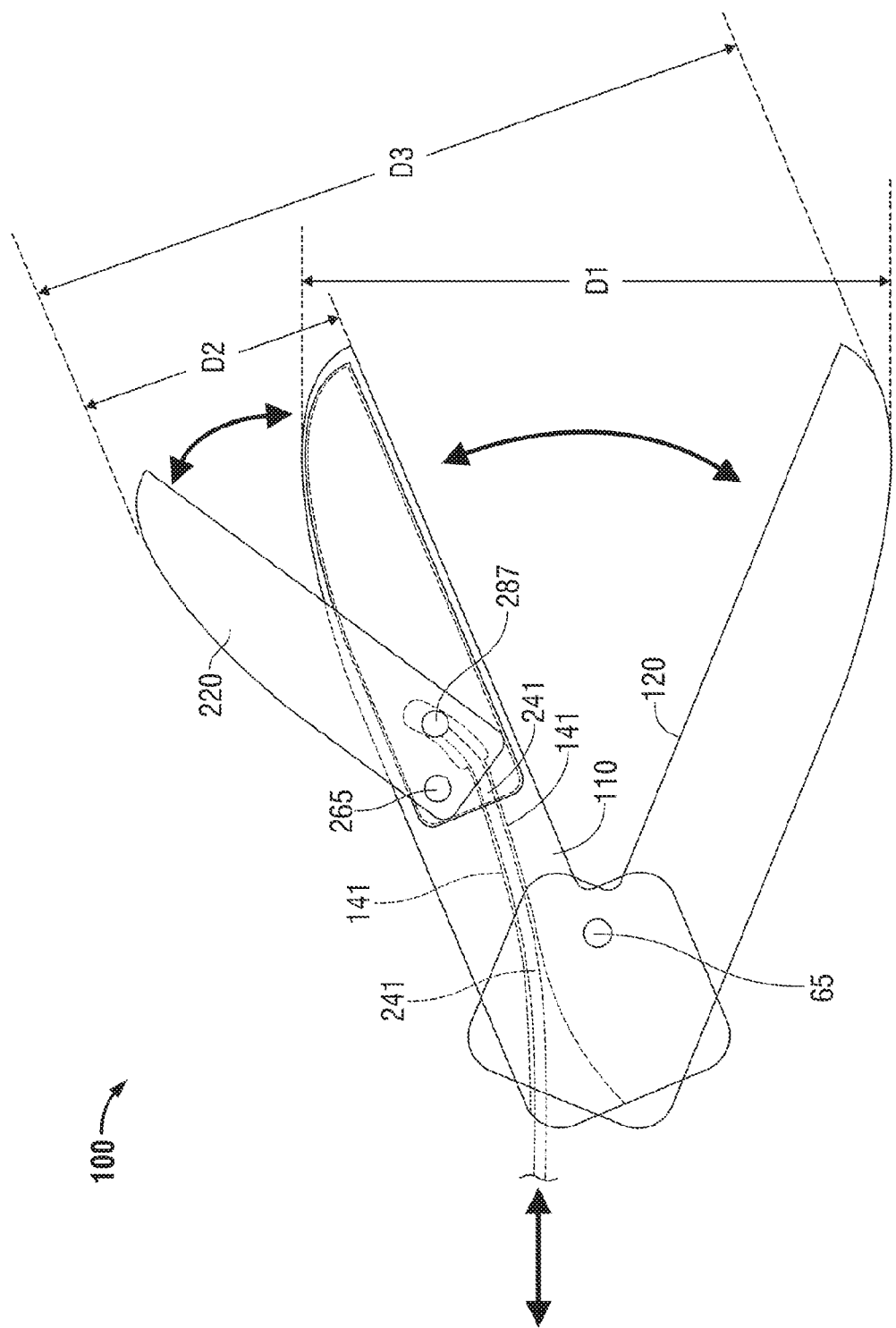
FIG. 3 is a right side-view of the multi-functional end effector assembly of FIG. 1 with the first device and second device in open condition.

Turning now to FIG. 3, first pivot 65 is disposed on a proximal end of multi-functional end effector assembly 100 and is configured to facilitate pivotal movement of the upper jaw member 110 and the lower jaw member 120. The upper and lower jaw members 110, 120 are configured to open to a first distance D1 with the shear blade 220 remaining in a fixed relationship with respect to the upper jaw member 110. Second pivot 265 is disposed on the proximal end of the shear blade 220 and connects the shear blade 220 to the upper jaw member 110. The actuation rod 241 is manipulated in a rod channel 141 defined in jaw member 110 and is configured to actuate the shear blade 220 about the second pivot 265 with respect to the upper jaw member 110. The shear blade 220 and upper jaw member 110 are configured to open to a second distance D2. With the upper and lower jaw members 110, 120 and the shear blade 220 positioned in open condition the forceps 10 are configured to open to a third distance D3. As such, the distal end of the forceps 10 may be used to separate and/or spread tissue a first distance D1, a second distance D2, a third distance D3 and any distance therebetween.

FIGS. 4A-4D are top-views of multi-functional end effector assemblies 400a-400d similar to the multi-functional end effector assembly 100 of the forceps in FIG. 1. The multi-functional end effector assemblies 400a-400d illustrate several arrangements of shear blades 420a-420d mated with corresponding curved upper jaw members 410a-410d, respectively. The arrangements shown in FIGS. 4A-4D are merely exemplifications of aspects, are not intended to be limiting, and the arrangements (and any modifications thereof) may be included in any surgical device to form a multi-functional surgical device as described herein.

Figure 4C:
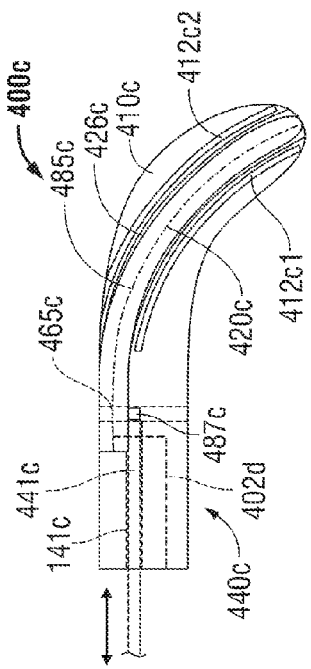
FIG. 4A-4D are top-views of various aspects of upper jaw members according to aspects of the present disclosure.
Figure 4D:
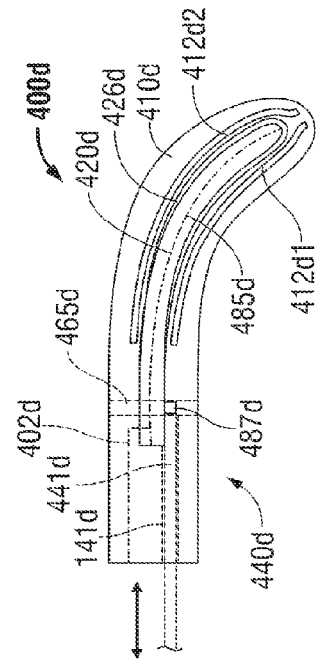
Figure 4A:
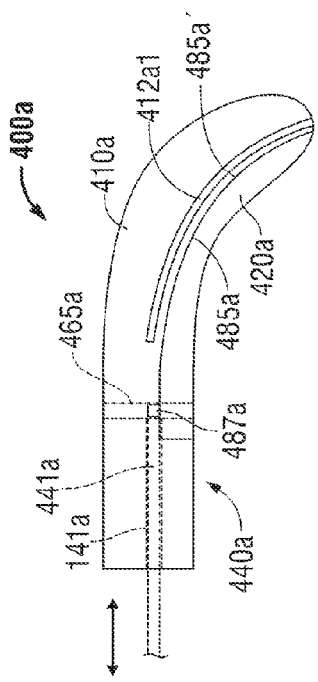
Figure 4B:
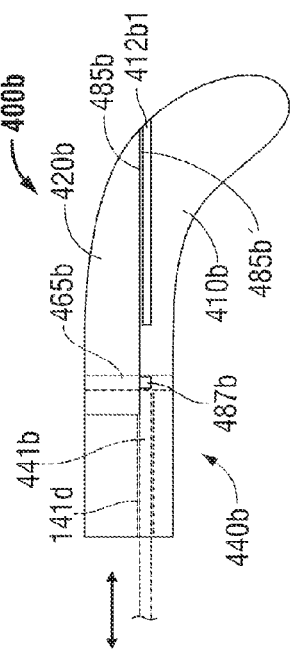

FIG. 4A illustrates a multi-functional end effector assembly 400a including a curved upper jaw member 410a mated with a curved shear blade 420a. FIG. 4B illustrates a multi-functional end effector 400b including a curved upper jaw member 410b mated with a straight shear blade 420b. FIGS. 4C and 4D illustrate multi-functional end effectors 400c, 400d including curved upper jaw members 410c, 410d mated with curved shear blades 420c, 420d each forming a curved electrosurgical cutter 485c. In FIG. 4D the curved upper jaw member 410d extends distally beyond the curved shear blade 420d.

FIGS. 4A-4D include actuation mechanisms 440a-440d, respectively, that each include a second pivot 465a-465d, an actuating rod pin 487a-487d and an actuation rod 441a-441d that slidingly engages the rod channel 141a-141d. The actuation mechanisms 440a-440d are configured to actuate the respective shear blades 420a-420d with respect to the upper jaw member 410a-410d about the respective second pivots 465a-465d. Actuating rod pins 487a-487d connect to shear blades 420a-420d and pivotably attach to actuation rods 441a-441d. Linear movement of the actuation rods 441a-441d in the rod channels 141a-141d drive the actuating rod pins 487a-487d which, in turn, pivots the shear blade 420a-420d about second pivots 465a-465d.

Actuation mechanisms 440a-440d may be formed of any suitable drive system or drive mechanism configured to translate movement of a user controlled actuation member on the proximal end of the forceps 10 (e.g., shear blade actuator 215 in FIG. 1) to movement of the respective shear blade 420a-420d of a multi-functional end effector assemblies 400a-400d. The actuation mechanisms 440a-440d may be configured to pivot the respective shear blades 420a-420d in a parallel manner such that the shear blade 420a-420d remain substantially parallel to the corresponding jaw member (e.g., upper or lower jaw member 110 and 120).

Actuating rod pins 487a-487d and/or second pivots 465a-465d may be individually assembled to form the actuation mechanisms 440a-440d. Alternatively, the actuating rod pins 487a-487d and/or the second pivots 465a-465d may be formed as part of the shear blades 420a-420d, the upper jaw members 410a-410d or both.

With reference to FIGS. 4A and 4B, upper jaw members 410a, 410b and the corresponding shear blades 420a, 420b are configured for mechanical cutting and/or electro-mechanical cutting as described hereinabove. In a closed condition, as illustrated in FIGS. 4A and 4B, the cutting surfaces (e.g., cutting edge 485a, 485b and/or corresponding fixed cutting edge 485a', 485b') may contact each other along a substantial portion of the abutting surfaces. Alternatively, the cutting edges 485a, 485b and the corresponding fixed cutting edges 485a', 485b' may not include the same bend.

With reference to FIGS. 4A-4D, electrosurgical energy delivery may be used in conjunction with mechanical cutting or electrosurgical energy may provide the primary (or only) means of cutting, as illustrated in FIGS. 4C-4D.

The multi-functional end effector assemblies 400a-400d may include one or more monopolar electrodes configured to deliver monopolar electrosurgical energy to tissue and/or one or more bipolar electrode pairs configured to delivery bipolar electrosurgical energy through tissue positioned therebetween. A monopolar electrode may be positioned on the upper jaw members 410a-410d, on at least a portion of the corresponding shear blades 420a-420d or both. Examples of electrodes on the upper jaw members 410a-410d include the fixed electrode 412a1 in FIG. 4A, the fixed electrode 412b1 in FIG. 4B, the first and/or second fixed electrodes 412c1, 412c2 in FIG. 4C and the first and/or second fixed electrodes 412d1, 412d2 in FIG. 4D. Examples of electrodes formed on or as part of the a shear blades 420a-420d include an articulating electrode 220a (See FIGS. 2A and 2B, as applied to FIGS. 4A and 4B), at least portion of the articulating cutting edge 285a forming an electrode (See FIGS. 2A and 2B, as applied to FIGS. 4A and 4B), and the electrosurgical cutter 485c, 485d in FIGS. 4C-4D.

In FIGS. 4C and 4D, the multi-functional end effector assemblies 400c, 400d may be configured for monopolar cutting, bipolar cutting or configured to selectively cut in monopolar and bipolar electrosurgical energy delivery modes. In monopolar mode, the respective shear blades 420c, 420d include an electrosurgical cutting edge 485c configured to deliver monopolar electrosurgical energy and cut tissue while the respective shear blades 420c, 420d are actuated between an open condition and a closed condition.

Electrosurgical energy is delivered to each electrodes 485c, 485d on the shear blade 420c, 420d through a suitable electrical connection formed between the shear blades 420c, 420d and an electrical contact or conductor 402c, 402d on the upper jaw member 410c, 410d. For example, as illustrated in FIGS. 4C and 4D, an electrical connection could be formed by a direct electrical connection, through an electrical connection formed adjacent or through the second pivot 465c, 465d, actuating rod pins 487c, 487d or actuation rods 441c, 441d or the electrical connection could be formed by any other suitable electrical connection device configured to provide an electrical connection (e.g., slip ring, slip contactor, etc. . . . )

In bipolar mode, at least one bipolar electrode pair is configured to deliver electrosurgical energy therebetween. The bipolar electrode pair may be selected from any two suitable electrodes, such as, for example and with respect to FIG. 4C, first fixed electrode 412c1, second fixed electrode 412c2 and the electrosurgical cutter 485c. In another aspect, the multi-functional end effector assembly 400c includes two bipolar electrode pairs. For example, first fixed electrode 412c1 and electrosurgical cutter 485c may form a first bipolar electrode pair and second fixed electrode 412c2 and electrosurgical cutter 485c may form the second bipolar electrode pair. Energy may be simultaneously delivered between the first and second bipolar electrode pairs or energy may be time proportioned therebetween.

The electrodes of each bipolar electrode pair are sufficiently spaced apart to prevent shorting between the electrodes and to define a target tissue positioned therebetween. For example, a bipolar electrode pair that includes an electrode on the upper jaw member 410a (e.g., fixed electrode 412a1) and an electrode on the shear blade 420a (e.g., electrode 220a, see FIGS. 2A and 2B) include a sufficient gap therebetween. The gap may be formed by providing sufficient spacing of the electrode on the upper jaw member 410a (e.g., spaced away from the shear blade 420a) and/or by providing sufficient spacing of the electrode on the shear blade 420a (e.g., spaced away from the electrode on the upper jaw member 410a). Similarly, a multi-functional end effector that includes a bipolar electrode pair with a first electrode disposed on the upper jaw member 410a and the second electrode formed by at least a portion of the shear blade 420a may provide spacing between the electrodes by positioning the fixed electrode away from the shear blade 420a-420d. In a monopolar energy delivery mode, a gap between the fixed electrode 412a1 and the cutting surface may not be desirable or necessary.

The multi-functional end effector assembly 400a in FIG. 4A also illustrates a curved upper jaw member 410a mated with a curved shear blade 420a. Upper jaw member 410a and shear blade 420a may be configured for mechanical cutting and/or electro-mechanical cutting as described hereinabove. In a closed condition the cutting edge 485a and fixed cutting edge 485a' may contact each other along a substantial portion of the length.

The multi-functional end effector assembly 400b in FIG. 4B illustrates a curved upper jaw member 410b mated with a straight shear blade 420b. Upper jaw member 410b and shear blade 420b may be configured for mechanical cutting and/or electro-mechanical cutting as described hereinabove. In a closed condition the cutting edge 485b and fixed cutting edge 485b' contact each other along a substantial portion of the length.

The multi-functional end effector assemblies 400c, 400d in FIGS. 4C and 4D, respectively, illustrate curved upper jaw members 410c, 410d mated with respective curved shear blades 420c, 420d. Upper jaw members 410c, 410d and respective shear blades 420c, 420d are configured for electrosurgical cutting and/or electro-mechanical cutting. In a closed condition, each shear blade 420c, 420d is positioned in the respective blade channel 426c, 426d formed in the corresponding upper jaw member 410c, 410d. In a closed condition, the outer surface of the upper jaw members 410c, 410d and the outer surface of the shear blades 420c, 420d form a uniformly curved outer surface of the multi-functional end effector assembly 400c, 400d. The inner surface of the shear blades 420c, 420d (i.e., the surface abutting the upper jaw member) include respective electrosurgical cutters 485c, 485d configured to perform non-contact and/or minimal-contact electrosurgical cutting.

Electrosurgical cutters 485c, 485d, are configured to deliver monopolar electrosurgical energy while transitioning from an open condition to a closed condition, as discussed hereinabove. Energization of the electrosurgical cutters 485c, 485d may be configured to be automatic delivered or manually selected. Manual selected energy delivery may include a clinician-controlled switch and/or selector (e.g., a foot operated controller, a switch or selector on the electrosurgical generator, and/or a switch or selector on the forceps 10).

Forceps 10 (See FIG. 1) may be configured to automatically enable the flow of electrosurgical energy to the electrosurgical cutters 485c, 485d by measuring one or more tissue parameters and enabling the flow of monopolar electrosurgical energy when the parameter(s) meets a condition with respect to a threshold value. For example, the shear blade actuator 215 may include a sensor (e.g., pressure sensor 215a, FIG. 1, or any other suitable sensor) configured to measure a parameter related to closing the shear blade 420c (e.g., the applied pressure). The pressure sensor 215a may include any pressure sensor such as a piezoelectric pressure sensor, strain gauge or any other suitable pressure sensing device. The measured pressure is compared to a threshold value and energy delivery may be automatically initiated when the measured pressure meets a condition indicative of compression of tissue between the shear blade 420c, 420d and the upper jaw member 410c. In another aspect, energy may be automatically delivered when the shear blade 420c transitions from an open condition to a closed condition.

In another aspect, tissue impedance is measured from, or between, any electrode or electrode pair. The measured tissue impedance may be used to determine the presence of tissue positioned between the shear blade 420c and the upper jaw member 410c or tissue impedance may be use to determine a parameter(s) related to the delivered energy (e.g., the power, voltage, current and/or duration of the energy).

Bipolar electrosurgical energy may be selectively delivered between any two of the first fixed electrodes 412c1, 412d1 the second fixed electrode 412c2, 412d2 and the electrosurgical cutters 485c, 485d. Bipolar electrosurgical energy may be delivered to ablate tissue while the electrosurgical cutters 485c, 485d deliver monopolar electrosurgical energy and electrosurgically cuts tissue. Alternatively, bipolar energy may be delivered between the electrosurgical cutters 485c, 485d and each of the first and second fixed electrodes 412c1, 412d1 and 412c2 and 412d2 in an initial treatment stage and the electrosurgical cutters 485c, 485d may deliver monopolar electrosurgical energy to cut tissue in a subsequent cutting stage.

In FIG. 4C, first and second fixed electrodes 412c1, 412c2 extend to the distal end of the upper jaw member 410c and the tip of the multifunctional end effector 400c may be used to coagulate or cauterize tissue by delivering electrosurgical energy in a bipolar manner therebetween. In FIG. 4D, first and second fixed electrodes 412d1, 412d2 extend to the distal end of the upper jaw member 410c and distal to the distal tip of the shear blade 420d.

Multi-Function Endoscopic Surgical Device

Referring now to FIG. 5A, a forceps 1000 for use with endoscopic surgical procedures includes a multi-functional end effector 500 is shown in accordance with aspects of the present disclosure.

Generally, forceps 1000 includes a housing 525, a handle assembly 530, a rotating assembly 580, and a multi-functional end effector assembly 500 that mutually cooperate to grasp, seal, and divide tubular vessels and vascular tissue and that cuts and/or severs patient tissue. The forceps 1000 includes a shaft 512 that has a distal end 616 dimensioned to mechanically engage the multi-functional end effector assembly 500 and a proximal end 514 that mechanically engages the housing 525.

The handle assembly 530 includes a fixed handle 550 and a movable handle 540. Fixed handle 550 is integrally associated with housing 525 and handle 540 is movable relative to fixed handle 550. Rotating assembly 580 is integrally associated with the housing 525 and is rotatable approximately 360 degrees in either direction about a longitudinal axis "A-A" defined through shaft 512. The housing 525 houses the internal working components of the forceps 1000.

Multi-functional end effector assembly 500, as illustrated in FIG. 5B, is attached to the distal end 516 of shaft 512 and includes a first surgical device and a second surgical device. First surgical device includes one or more tissue treatment members to provide a primary function of the multi-functional end effector 500. The second surgical device includes one or more tissue treatment members to provide a secondary function of the multifunctional end effector, wherein the first and second devices are independently operable and the primary and secondary functions are different. As discussed herein, the first surgical device is an actuating device configured to seal tissue and the second surgical device is an actuating device configured to cut/sever tissue.

In this particular aspect, the tissue treatment members of the first surgical device is an actuating device with includes a pair of opposing jaw members (e.g., upper jaw member 510 and lower jaw member 520) that are pivotably connected and movable relative to one another. Upper jaw member 510 and lower jaw member 520 each include an electrically conductive sealing surface 512a and 512b, respectively, disposed thereon to grasp and seal tissue positioned therebetween. The tissue treatment members of the second surgical device include the upper jaw member 510 and a shear blade 620 pivotably connected and movable relative to one another about a second pivot 665 to cut and/or shear tissue. The second surgical device may cut and/or shear tissue by mechanical cutting, electrical cutting or electro-mechanical cutting as discussed hereinabove. The first surgical device and second surgical device may operate independently, or may operate in cooperation with each other.

The construction of each upper and lower jaw member 510, 520 includes an electrically conductive sealing surface 512a, 512b, similar to the electrically conductive sealing surfaces 112a, 112b described hereinabove with respect to FIGS. 1 and 2. The functionality and construction of the upper and lower jaw members 510, 520 is similar to the upper and lower jaw members 110, 120 described hereinabove or the construction may be similar to other forceps used for endoscopic surgical procedures.

Figure 6C:
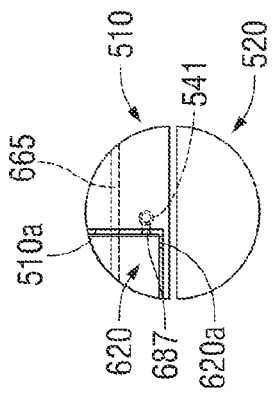
FIGS. 6C and 6D are front-views of the multi-functional end effectors in FIGS. 6A and 6B, respectively.
Figure 6D:
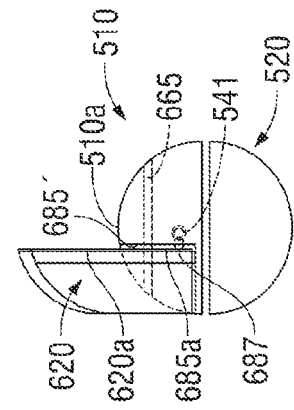
Figure 6A:
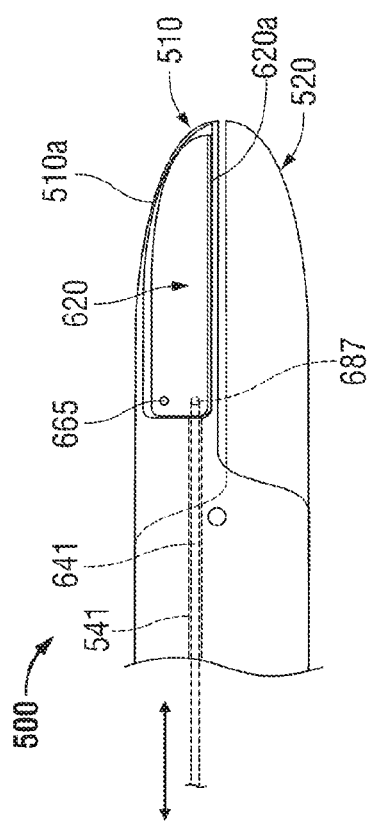
FIGS. 6A and 6B are side-views of the multi-functional end effector of FIG. 5A in closed and open conditions, respectively.

Movable handle 540 of handle assembly 530 is ultimately connected to a drive assembly (not shown) to impart movement of the jaw members 510 and 520 from an open condition, as illustrated in FIG. 5A, to a clamped or closed condition, as illustrated in FIGS. 6A and 6C. The lower end of the movable handle 540 includes a flange 590 extending proximally therefrom. Flange 490 is disposed within fixed handle 550 to releasably lock the movable handle 540 relative to the fixed handle 550.

Forceps 1000 includes a switch 555 disposed on housing 525 that operates substantially as described above with reference to switch 50 of forceps 10 (see FIG. 1). Although depicted on a proximal end of housing 525 in FIG. 5A, switch 555, or a similar type switch, may be disposed on any suitable portion of the housing 525 and, thus, FIG. 5A is not intended to be limiting with respect to the location of switch 555 relative to housing 525. For example, switch 555 may be disposed anywhere on housing 525 between its distal and proximal ends such that switch 555 is accessible to the user. Switch 555 operates substantially as described above with reference to switch 50 of FIG. 1 and will only be discussed to the extent necessary to describe the differences between various aspects.

Switch 555 is configured to be depressed by a user relative to housing 525 to meet any one or more thresholds as a function of displacement of switch 555 that, as described above with reference to switch 50. For example, switch 555 may generate a first tactile response corresponding to a complete grasping of tissue sensed between jaw members 510 and 520 and a second tactile response upon additional depression of switch 555 relative to housing 525 corresponding to a signal being generated to the electrosurgical generator to supply electrosurgical energy to the jaw members 510 and 520.

One (or both) of the upper jaw member 510 and the lower jaw member 520 may include a knife channel (e.g., an upper knife channel 515a and/or lower knife channel 515b, respectively) configured to facilitate reciprocation of a knife 585 therethrough. In this particular aspect, a complete knife channel 515 is formed by two opposing channel halves 515a and 515b associated with respective jaw members 510 and 520. The tissue grasping portions of the jaw members 510 and 520 are generally symmetrical and include similar component and features that cooperate to affect the grasping and sealing of tissue.

Figure 6B:
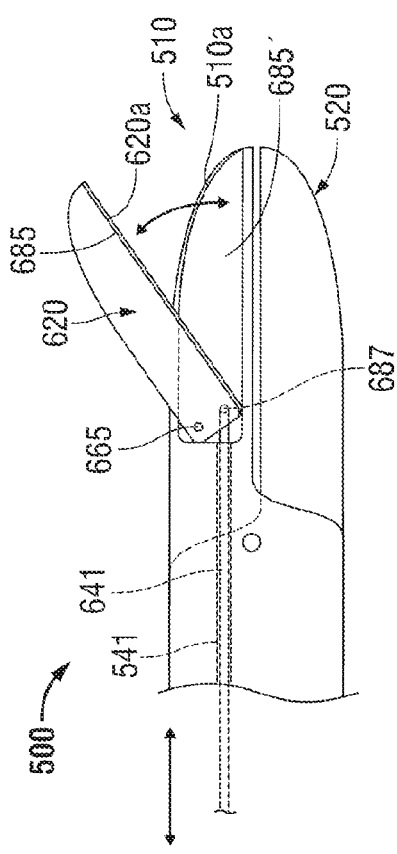

Shear blade actuator 615 is configured to actuate the shear blade 620 between a closed condition, as illustrated in FIGS. 6A and 6C, and an open condition, as illustrated in FIGS. 5, 6B and 6D. Positioning the shear blade actuator 615 in the most proximal position, as illustrated in FIG. 5A, closes the shear blade 620 with respect to the upper jaw member 510 and positioning the shear blade actuator 615 in the most distal position opens the shear blade 620 with respect to the upper jaw member 510.

Turning now to FIGS. 6A-6D, FIGS. 6A and 6B are side-views of the multi-functional end effector assembly 500 illustrate in FIG. 5A in closed and open conditions, respectively. FIGS. 6C and 6D are front-views of the distal end of the multi-functional end effector assemblies 500 of FIGS. 6A and 6D, respectively. In a closed condition, the lower jaw member 520 is generally symmetrical with the upper jaw member 510 mated with a closed shear blade 620. The generally symmetrical shape facilitates insertion and use in an endoscopic surgical procedure.

The shear blade 620 is configured to pivot about the second pivot 665 to an open condition, as illustrated in FIGS. 6B and 6D. The upper jaw member 510 and the shear blade 620 form a shearing/cutting interface therebetween. As discussed hereinabove, the shearing/cutting interface between the upper jaw member 510 and shear blade 620 may be mechanical, electrical and/or electro-mechanical or forceps 1000 may be configured for selection between mechanical cutting, electrical cutting or electromechanical cutting.

With reference to FIG. 6D, cutting edges 685, 685' may be formed from any suitable material, such as, for example, metal, ceramic or plastic. The cutting edge 685 and/or the fixed cutting edge 685' may include any suitable cutting surface, such as, for example, a straight and/or smooth finished surface, a sharpened edge, a rounded edge, a beveled edge or a serrated finished surface. To facilitate cutting, the cutting edge 685 and/or the fixed cutting edge 685' may bend slightly toward each other. The material, finished surface and/or curvature of the cutting edges 685a, 685a' need not be the same to provided a suitable cutting interface therebetween. The cutting edge 685 and the fixed cutting edge 685' may be formed and fitted such that the cutting edge 685, 685' remain in contact while the shear blade 620 actuates between an open condition and a closed condition.

As discussed hereinabove, multi-functional end effector assembly 500 may be configured for mechanical tissue cutting, electrical tissue cutting and/or electromechanical tissue cutting. In FIGS. 6C and 6D, multi-functional end effector assembly 500 includes a fixed electrode 510a disposed on the upper jaw member 510 and an electrode 620a disposed on the shear blade 620. Additional electrodes may be disposed or formed on the shear blade 620 and/or the upper jaw member 510 and the electrodes may be configured to delivery electrosurgical energy in a monopolar or bipolar fashion.

Figure 7C:
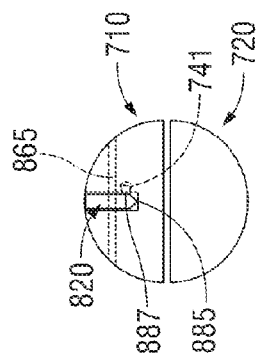
FIGS. 7C and 7D are front-views of the multi-functional end effectors in FIGS. 7A and 7B, respectively.
Figure 7D:
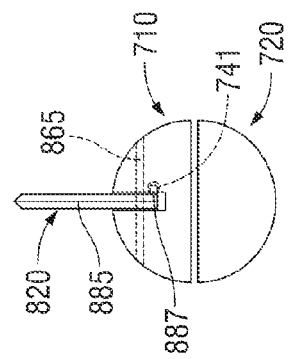
Figure 7A:
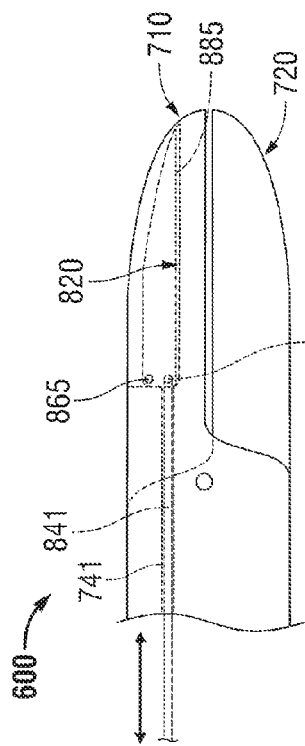
FIGS. 7A and 7B are side-views of another aspect of a multi-functional end effector in closed and open conditions, respectively.
Figure 7B:
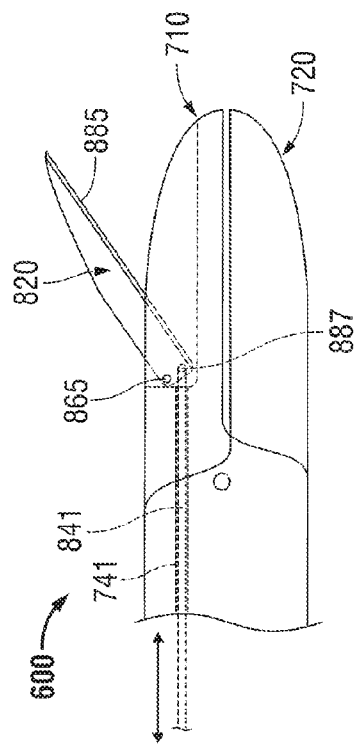

FIGS. 7A-7D illustrate a multi-functional end effector 700 that includes a second device configured to facilitate tissue cutting using monopolar electrosurgical energy. FIGS. 7A and 7B are side-views of the multi-functional end effector assembly 700 in a closed condition (FIG. 7A) and an open condition (FIG. 7B) and FIGS. 7C and 7D are front-views of the distal end of the multi-functional end effector assembly 700 of FIGS. 7A and 7B, respectively. In a closed condition, lower jaw member 720 is generally symmetrical with the upper jaw member 710 mated with endoscopic shear blade 820. The generally symmetrical shape facilitates insertion and use in endoscopic surgical procedures.

Shear blade 820 is configured to electrosurgically cut tissue positioned between the shear blade 820 and the upper jaw member 710. Cutting edge 885 on the lower surface of the shear blade 820 forms a monopolar electrode configured to deliver electrosurgical energy to cut tissue. Electrosurgical system also includes a grounding electrode (not explicitly shown) positioned on the patient and configured to return the monopolar electrosurgical energy delivered by the cutting edge 885 to the electrosurgical generator (see electrosurgical generator 1, FIG. 1).

Cutting edge 885 may be formed from, or coated with, any suitable conductive material, such as, for example, metal, stainless steel or silver. Cutting edge 885 may have a sharpened edge, rounded edge, beveled edge, serrated edge or any suitable shape that facilitates cutting of tissue. Shear blade 820, cutting edge 885 and the upper and low jaw members 710, 720 and may be straight or curved and may include various shapes along their length and/or at their tip.

Figure 8A:
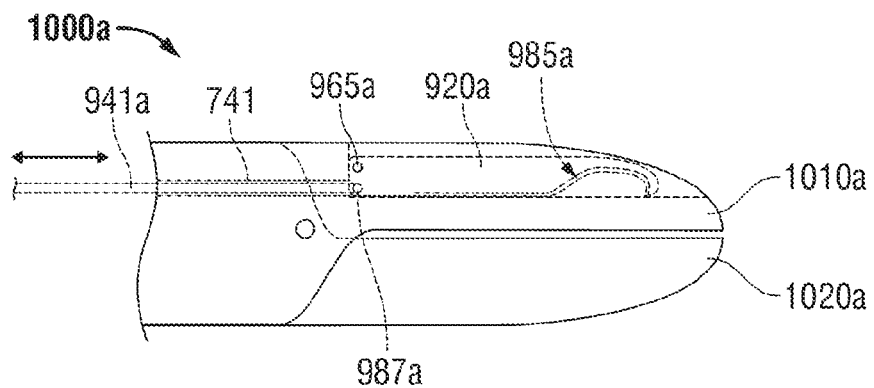
FIGS. 8A-8E are side-views and top-views of multi-functional end effectors according to other aspects of the present disclosure.
Figure 8B:
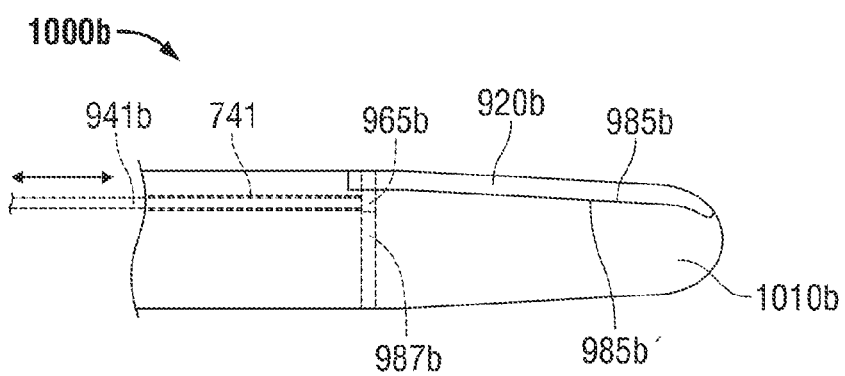
Figure 8C:
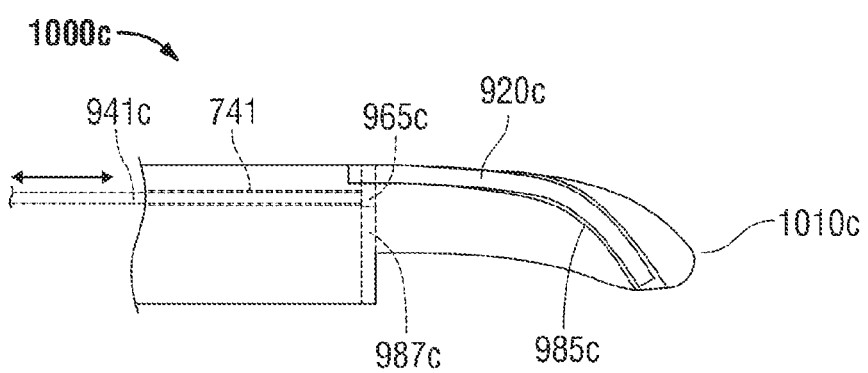
Figure 8D:
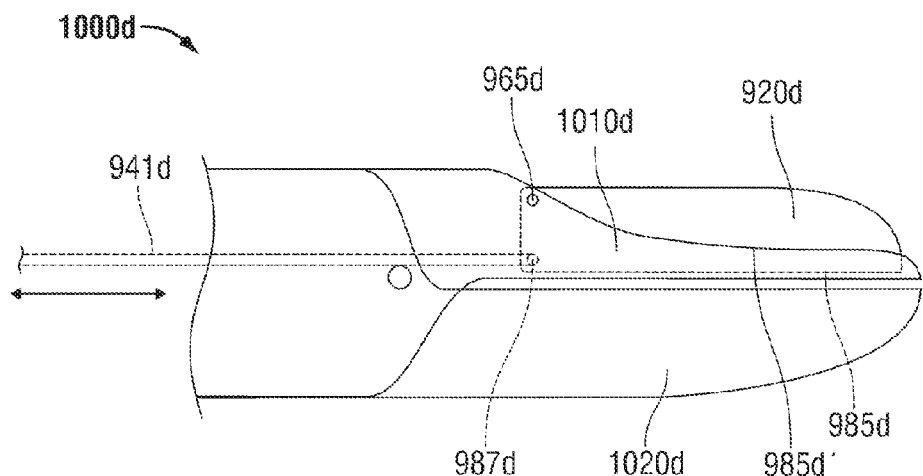
Figure 8E:
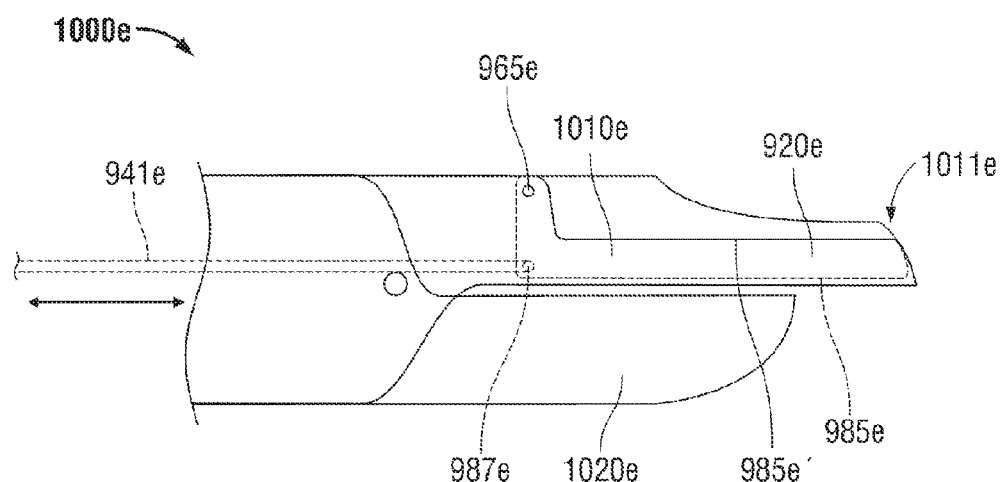

FIGS. 8A-8E are illustrations of various aspects of multi-functional end effector assemblies 1000a-1000e with FIGS. 8A, 8D and 8E being side views and FIGS. 8B and 8C being top views. The multi-functional end effector assemblies 1000a-1000e may be adapted to be used with the open surgical device illustrated in FIG. 1, the endoscopic surgical device illustrated in FIG. 5A or the aspects contained herein may be adapted for use with any other surgical device.

FIG. 8A includes a shear blade 920a having a hooked portion 985a on the distal end thereof. Hooked portion 985a may be used for grasping and/or hooking tissue during a surgical procedure or during the delivery of electrosurgical energy to tissue. Hooked shear blade 920a is similarly positioned with respect to the upper jaw member 1010a as the shear blade 820 is positioned to upper jaw member 710 illustrated in FIGS. 7A-7D.

FIG. 8B includes a curved shear blade 920b wherein the curvature of the curved shear blade 920a is substantially similar to the curvature of the distal end of the multi-functional end effector assembly 1000b. Shear blade 920b may be configured for mechanical cutting and/or electromechanical cutting as discussed hereinabove.

FIG. 8C also includes a curved shear blade 920c wherein the curvature of the shear blade 920c is greater than the curvature of the multi-functional end effector assembly 1000c. Curved shear blade 920c may be used for monopolar electrosurgical cutting as discussed hereinabove with respect to FIGS. 4C and 4D.

FIGS. 8D and 8E are non-symmetrical, multi-functional end effector assemblies 1000d, 1000e wherein the respective upper jaws members 1010d, 1010e and lower jaw members 1020d, 1020e lack symmetry with respect to on another. In FIG. 8D the upper jaw member 1010d includes a downward sloping upper surface with a thickness less than the thickness of the shear blade 920d and less than the thickness of the lower jaw member 1020d. The articulating cutting edge 985d and the sloped fixed cutting edge 985d' form a cutting surface therebetween.

Actuating rod pin 987d pivotably attaches actuation rod 941d to shear blade 920d and shear blade 920d pivots about second pivot 965d when the shear blade actuator (not explicitly shown) actuates the actuation rod 941d. The downward sloping portion of the fixed cutting edge 985d' may be preferable for cutting due to the angle between the fixed cutting edge 985d' and the articulating cutting edge 985d.

In FIG. 8E, the multi-functional end effector assembly 1000e includes an upper jaw member 1010e and a shear blade 920e sized differently than the lower jaw member 1020e. The distal portion 1011e of the upper jaw member 1010e and the shear blade 920e extend beyond the distal end of the lower jaw member 1020e such that the overall thickness of the end effector assembly 1000e at the distal end thereof is substantially thinner than the overall or general thickness of the end effector assembly 1000e. The thin distal end 1011e may be advantageous for cutting or severing tissue in cavities or in narrow areas during a surgical procedure.

Figure 9A:
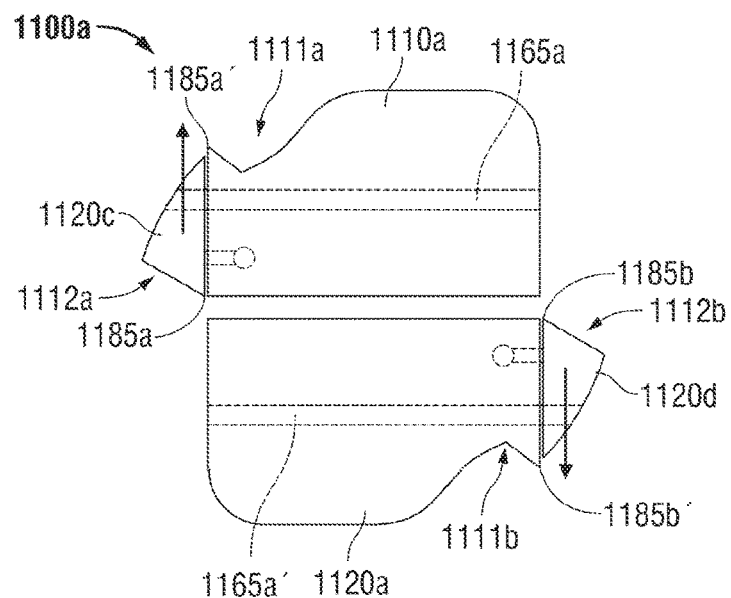
FIGS. 9A and 9B are rear-views of various aspects of multi-functional end effectors in closed conditions.
Figure 9B:
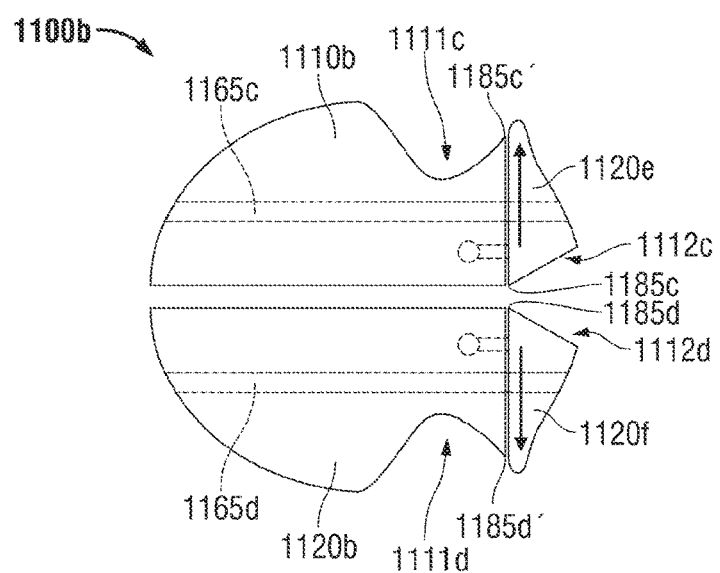

FIGS. 9A and 9B illustrate another aspect of shear blades 1120c-1120f, according to the present disclosure associated with respective jaw members (e.g., shear blades 1120c, 1120e associated with upper jaw members 1110a, 1110b and shear blades 1120d, 1120f associated with lower jaw members 1120a, 1120b. Any suitable combination or association that positions one or more secondary surgical devices (e.g., shear blade) on an end effector is hereby contemplated. FIGS. 9A and 9B illustrate two such combinations.

As illustrated in FIG. 9A, the position of shear blades 1120c, 1120d may not be symmetrical with respect to respective jaw members 1110a, 1120a and may provide shear blades 1120c, 1120d on opposite sides of the multifunctional end effector assembly 1100a and/or on each of the jaw members 1110a, 1120a. Dimensionally, the shear blades 1120c, 1120d are substantially similar.

As illustrated in FIG. 9B, the shear blades 1120e, 1120f may be symmetrical with respect to the jaw members 1110b, 1120b with shear blades 1120e, 1120f on the same side of the multi-functional end effector assembly 1100b.

As further illustrated in FIGS. 9A and 9B, the upper and lower jaw members 1110a, 1110b and 1120a, 1120b and the corresponding shear blades 1120c, 1120e and 1120d, 1120f may include one or more contours that form a shaped interface between each shear cutting surface (e.g., defined by respective cutting edges and fixed cutting edges 1185a and 1185a'; 1185b and 1185b', 1185c and 1185c', 1185d and 1185d'). For example, upper jaw members 1110a, 1110b and lower jaw members 1120a, 1120b may each include corresponding recessed portions 1111a, 1111c and 1111b, 1111d with dimensions that form a sharpened tip along each of the fixed cutting edges 1185a', 1185b', 1185c', 1185d'. Similarly, each of the shear blades 1120c-1120f may include a corresponding angled portions 1112a-1112d adjacent the cutting edges 1185a-1185d with dimensions that form a sharpened tip on each cutting edge 1185a-1185d. As such, the recessed portions 1111a-1111d and the angled portions 1112a-1112d are configured to form corresponding sharpened edges along each of the cutting edges 1185a'-1185d' and 1185a-1185d to facilitate cutting therebetween.

A contour formed by the shear blades 1120e-1120f and a corresponding contour formed on jaw members 1110b, 1120b together may form a smooth transition along the outer surface of the multi-functional end effector 1100b between the shear blades 1120e-1120f and the corresponding jaw members 1110b, 1120b. For example, as illustrated in FIG. 9B, the recessed portions 1111c, 1111d that form the sharpened tip along each of the fixed cutting edges 1185c', 1185d' while in a closed condition mates with the curvature of the shear blade 1120e, 1120f thereby forming a smooth transition therebetween.

Figure 10A:
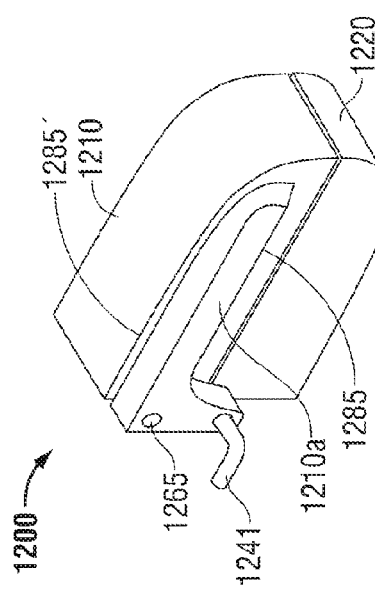
FIG. 10A is a right, perspective view of another aspect of a multi-functional end effector with an external actuation rod.
Figure 10B:
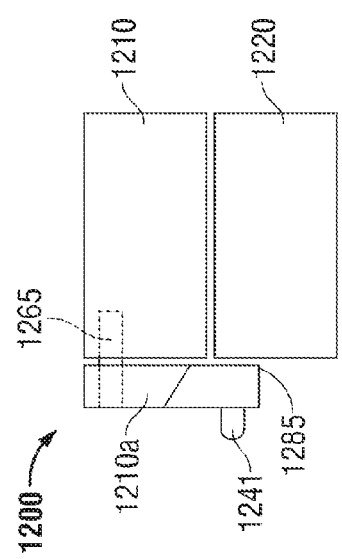
FIG. 10B is a front-view of the multi-functional end effector in FIG. 10A.

FIGS. 10A and 10B illustrate another aspect of a multi-functional end effector assembly 1200 that includes rectangular-shaped upper and lower jaw members 1210, 1220 and an external, side-mounted shear blade 1210a mated to the upper jaw member 1210. The externally side-mounted shear blade 1220b includes a pivot pin 1265 pivotally connected to the upper jaw member 1210 and an externally mounted actuation rod 1241. Fixed cutting edge 1285' is formed along an exterior edge of the rectangular-shaped upper jaw member 1210 and interfaces with articulating cutting edge 1285 to form scissors therebetween.

Figure 11A:
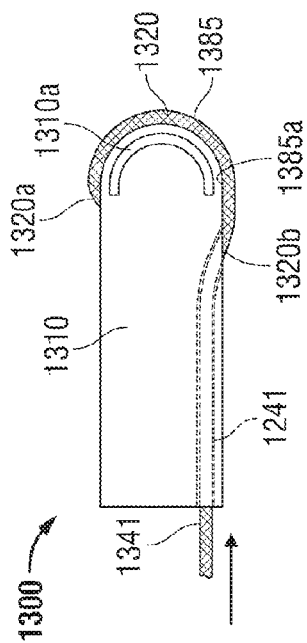
FIGS. 11A and 11B are top-views of another aspect of a multi-functional end effector with a loop electrode in closed and open conditions, respectively.
Figure 11B:
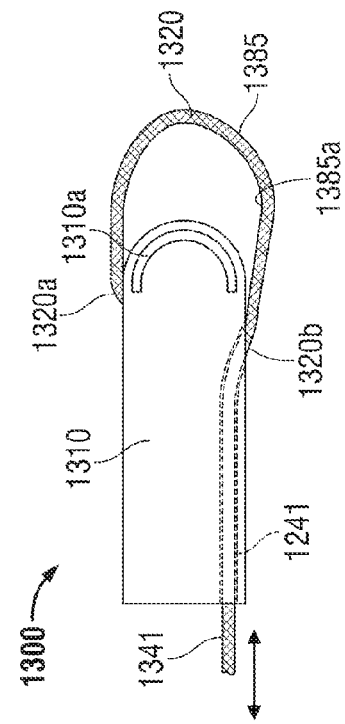

FIGS. 11A and 11B are top-views of a multi-functional end effector assembly 1300 according to another aspect of the present disclosure wherein the second actuating device is a loop electrode 1320. Loop electrode 1320 actuates between a retracted position, as illustrated in FIG. 11A, and a deployed position, as illustrated in FIG. 11B. The distal end 1320a of the loop electrode 1320 is secured to the upper jaw member 1310 and the proximal end 1320b of the loop electrode 1320 is secured to the actuation rod 1341. Actuation rod 1341 is actuated within the actuation rod channel 1241 formed in the upper jaw member 1310 by a second device actuator (not explicitly shown, see shear blade actuator 215, 615 illustrated in FIGS. 1 and 5, respectfully) mounted on the housing 12a of the forceps 10.

Loop electrode 1320 includes a treatment member shear surface 1385. Treatment member shear surface 1385 may be configured to delivery electrosurgical energy in a retracted position (See FIG. 11A). The clinician energizes the loop electrode 1320 in the retracted position and utilizes the distal end of the multi-functional end effector assembly 1300 to cauterize, coagulate and/or cut tissue.

In use, loop electrode 1320 may be deployed from a retracted condition (See FIG. 11A) to a "deployed" condition (See FIG. 11B illustrating one "deployed" condition). As described herein, a "deployed" condition is any condition wherein the loop electrode 1320 is not in the retracted condition. A clinician may position tissue between any portion of the loop electrode 1320 and the upper jaw member 1310 and subsequently retract the loop electrode 1320 to secure the tissue therebetween (e.g., a clinician may utilize the loop electrode 1320 to "snare" or grasp tissue between the upper jaw member 1310 and the loop electrode 1320). Inner surface 1385a of the treatment member shear surface 1385 contacts the tissue and loop electrode 1320 delivers electrosurgical energy to the secured tissue in a monopolar or bipolar mode. Loop electrode 1320 may also include a sharpened edge that when retracted from a deployed condition to the retracted condition cuts tissue as the loop electrode 1320 is retracted.

In a monopolar energy delivery mode, the electrosurgical energy delivered to tissue by the loop electrode 1320 is returned to the electrosurgical generator through an electrosurgical return pad (not explicitly shown) positioned on the patient. In a bipolar energy delivery mode, the electrosurgical energy is delivered to the tissue positioned between the loop electrode 1320 and a second bipolar electrode 1310a formed on the upper jaw member 1310. The second bipolar electrode 1310a may be positioned at any suitable position on the upper jaw member 1310 or the lower jaw member (not explicitly shown). Alternatively, a portion of the first surgical device may be configured as the second bipolar electrode.

The loop electrode 1320, as described hereinabove, may be associated with the upper jaw member 1310, the lower jaw member (not explicitly shown) or the loop electrode 1320 may be related with both the upper jaw member and the lower jaw member.

Loop electrode 1320 (or any of the second devices described herein) may also be utilized to coagulate, cauterize or ablate tissue. For example, in a retracted condition the clinician may position the distal end of the multi-functional end effector 1300 adjacent target tissue such that at least a portion of the loop electrode 1320 is sufficiently positioned with respect to the target tissue to deliver electrosurgical energy and coagulate, cauterize and/or ablate the target tissue. Subsequently, the clinician may position the loop electrode to cut tissue as described above.

Figure 12A:
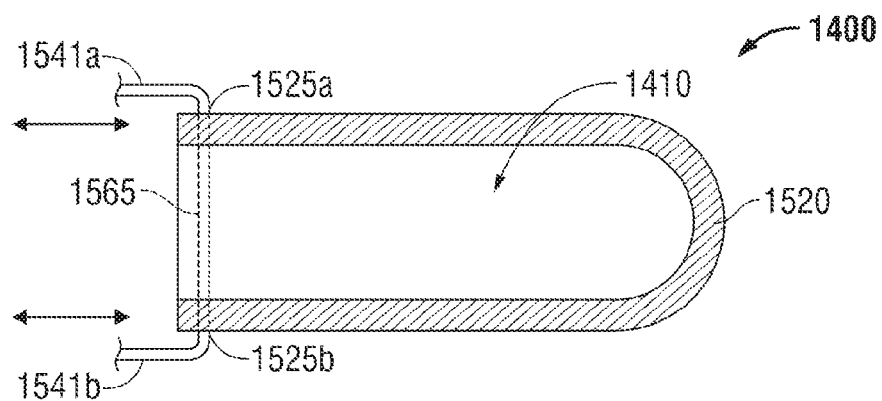
FIG. 12A is a top-view of another aspect of a multi-functional end effector with a u-shaped electrode.
Figure 12B:
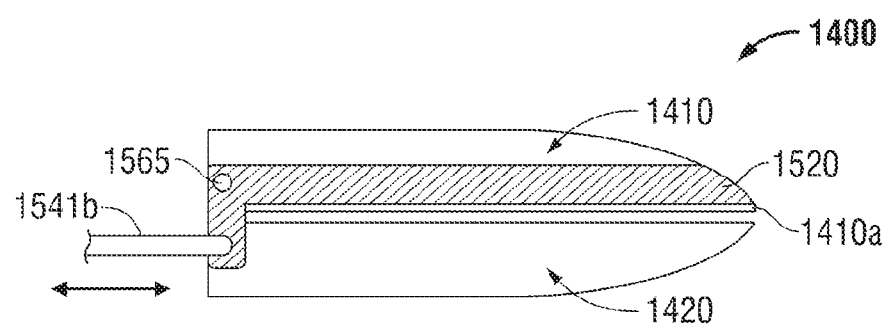
FIGS. 12B and 12C are side-views of the multi-functional end effector of FIG. 12A in closed and open conditions, respectively.
Figure 12C:
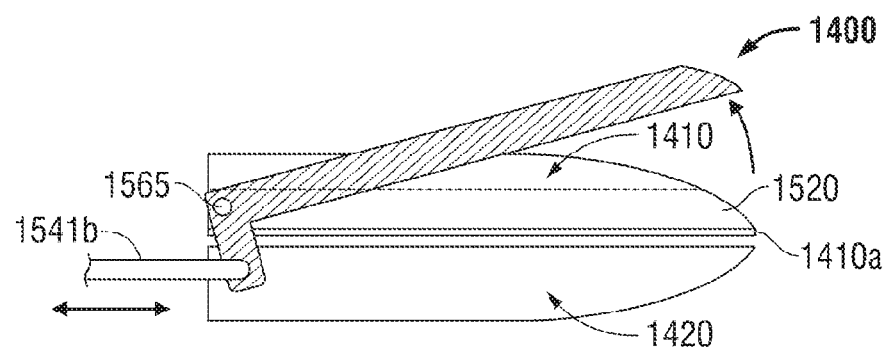

A multi-functional end effector assembly 1400, according to another aspect of the present disclosure, is shown in FIGS. 12A-12C and includes a U-shaped electrode 1520 associated with the upper jaw member 1410. FIG. 12A is a top-view and FIGS. 12B and 12C are side-views of the multi-functional end effector assembly 1400. U-shaped electrode 1520 is actuated between a close condition, as illustrated in FIGS. 12A and 12B, and an open condition, as illustrated in FIG. 12C. Second pivot 1565 extends through the proximal end of the upper jaw member 1410 and pivotably attaches to the first and second proximal ends 1525a, 1525b of the U-shaped electrode 1520 and the first and second proximal ends 1525a, 1525b of the U-shaped electrode 1520 pivot about the second pivot 1565.

First and second actuation rods 1541a, 1541b each attach to corresponding proximal ends 1525a, 1525b of the U-shaped electrode 1520 and are configured to actuate the U-shaped electrode 1520 between a closed condition (See FIGS. 12A and 12B) and an open condition (See FIG. 12C).

As illustrated in FIGS. 12A-12C, first and second actuation rods 1541*a*, 1541*b* are externally mounted. In another aspect, first and second actuation rods are actuated within actuation rod channels (not explicitly shown) formed in the upper jaw member 1410. Actuation rods 1541*a*, 1541*b* are actuated by a second device actuator (not explicitly shown, see shear blade actuator 215, 615 illustrated in FIGS. 1 and 5, respectfully) mounted on the handle portion of the device.

In use, U-shaped electrode 1520 deployed from a closed condition (See FIGS. 12A and 12B) to an open condition (See FIG. 12C illustrating one open condition) wherein the open condition is any position wherein the U-shaped electrode 1520 is not in the closed condition. A clinician may position tissue between any portion of the U-shaped electrode 1520 and the upper jaw member 1410 and subsequently actuate the U-shaped electrode 1520 to secure the tissue therebetween. (e.g., a clinician may utilize the U-shaped electrode 1520 to grasp tissue between the upper jaw member 1410 and the U-shaped electrode 1520). U-shaped electrode 1520 may delivery electrosurgical energy to the secured tissue in a monopolar or bipolar mode. U-shaped electrode 1520 may be pivoted from an open condition to the closed condition thereby cutting the tissue as the U-shaped electrode are actuated.

In a monopolar energy delivery mode, the electrosurgical energy delivered to tissue by the U-shaped electrode 1520 is returned to the electrosurgical generator through an electrosurgical return pad (not explicitly shown) positioned on the patient. In a bipolar energy delivery mode, the electrosurgical energy is delivered to tissue positioned between the U-shaped electrode 1520 and a second bipolar electrode 1410*a* formed on the upper jaw member 1410. The second bipolar electrode 1410*a* may be positioned at any suitable position on the upper jaw member 1410 or the lower jaw member 1420. Alternatively, a portion of the first surgical device may be configured as the second bipolar electrode.

The U-shaped electrode 1520, as described hereinabove, may be associated with the upper jaw member 1410, the lower jaw member 1420 or a U-shaped electrode according to the present disclosure may be positioned relative to both the upper and lower jaw members 1410, 1420.

In yet another aspect of the present disclosure a multi-functional end effector within the spirit of the present disclosure include a first surgical device, a second surgical device and a third surgical device. For example, the first surgical device may include a vessel sealing device and the second and third surgical devices may be selected from any two of a first shear blade, a second shear blade, a loop electrode and a U-shaped electrode according to aspects of the present disclosure.

As discussed hereinabove, the surgical instruments (forceps 10, 1000) include an end effector (e.g., end effector assembly 100, 500) mechanically coupled to a housing (e.g., shafts 12*a* and 12*b*; housing 525), with a first actuating device and a second actuating device. The first actuating device including a first treatment member (e.g. upper jaw member 110, 510) and a second treatment member (e.g., low jaw member 120, 520) configured to move relative to one another about a first pivot (e.g., pivot 65, 565). The first and second treatment members are adapted to selectively connect to a source of electrosurgical energy (e.g., electrosurgical generator 1) and configured to seal tissue positioned between the first treatment member and the second treatment member. The second actuating device includes a third treatment member (e.g., shear blade 220, 620, etc. . . . ) integrally associated with the first actuating device and configured to move relative to the first treatment member about a second pivot (e.g., second pivot 265, 665), the second pivot (e.g., second pivot 265, 665) being different than the first pivot (e.g., pivot 65, 565). The third treatment member is adapted to selectively connect to a source of electrosurgical energy (e.g., generator 1) wherein the second actuating device is configured to cut tissue positioned between the first treatment member (e.g., upper jaw member 110, 510) and the third treatment member (e.g., shear blade 220, 620). An outer portion of the first actuating device and an outer portion of the second actuating device form a portion of an outer housing of the end effector. Housing (e.g., shafts, 12*a* and 12*b*; housing 525) includes a first actuator (e.g., handles 15 and 17; handle assembly 530) mechanically coupled to the first actuating device and configured to impart movement to the first actuating device. Housing (e.g., shafts, 12*a* and 12*b*; housing 525) also includes a second actuator (e.g., shear blade actuator 215, 615) mechanically coupled to the second actuating device and configured to impart movement to the second actuating device. A switch (e.g., switch 50, 555) is configured to select the mode of operation for the surgical instrument.

In use, the switch (e.g., switch 50, 555) may be configured to select a bipolar sealing mode wherein the first treatment member receive electrosurgical energy at a first potential, the second treatment member receive electrosurgical energy at a second potential different than the first potential. The first actuating device provides treatment to tissue positioned between the first treatment member and the second treatment member to seal tissue in a bipolar fashion.

Switch (e.g., switch 50, 555) may also be configured to select a bipolar cutting mode wherein the first and second treatment members receive electrosurgical energy at a first potential, the third treatment member receives electrosurgical energy at a second potential different than the first potential. The second actuating device provides treatment to tissue positioned between the first treatment member and the second treatment member to cut tissue in a bipolar fashion.

Switch (e.g., switch 50, 555) may further be configured to select a monopolar sealing mode wherein the first treatment member and second treatment member receive electrosurgical energy at a first potential and electrically cooperate with a remotely disposed return pad engaged to patient tissue. The first actuating device provides treatment to tissue positioned between the first and second treatment members to seal tissue in a monopolar fashion.

Switch (e.g., switch 50, 555) may even be further configured to select a monopolar cutting mode wherein the third treatment member receives electrosurgical energy at a first potential and electrically cooperates with a remotely disposed return pad engaged to patient tissue. The second actuating device provides treatment to tissue positioned between the first treatment member and the third treatment member to cut tissue in a monopolar fashion.

Finally, switch (e.g., switch 50, 555) may be configured to select between at least two of bipolar sealing between the first and second treatment members, monopolar sealing between the first and second treatment members and a remotely disposed return pad engaged to patient tissue, bipolar cutting between the third treatment member and the first and second treatment members, and monopolar cutting between the third treatment member and the remotely disposed return pad engaged to patient tissue.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects. Those skilled in the art will envision other modifications within the scope and spirit of the claims appended hereto.

What is claimed is:

1. A surgical instrument, comprising:
an end effector including:
a first actuating device including a first treatment member and a second treatment member configured to move relative to one another to enable positioning of tissue therebetween, each of the first and second treatment members adapted to selectively connect to a source of electrosurgical energy, wherein the first actuation device is configured to seal tissue positioned between the first treatment member and the second treatment member using electrosurgical energy;
a second actuating device including a third treatment member configured to move relative to the first treatment member independent of the relative movement of the first and second treatment members, the third treatment member adapted to selectively connect to a source of electrosurgical energy, wherein the second actuating device is configured to treat tissue positioned between the first treatment member and the third treatment member using electrosurgical energy;
a first actuator operably coupled to the first actuating device and configured to impart movement to the first actuating device;
a second actuator operably coupled to the second actuating device and configured to impart movement to the second actuating device; and
a switch configured to select a mode of operation for selectively energizing at least one of the first, second, or third treatment members.

2. The surgical instrument of claim 1, wherein the switch is configured to select a bipolar sealing mode wherein the first treatment member receives electrosurgical energy at a first potential and the second treatment member receives electrosurgical energy at a second potential such that tissue positioned between the first treatment member and the second treatment member is sealed using bipolar electrosurgical energy.

3. The surgical instrument of claim 1, wherein the switch is configured to select a bipolar cutting mode wherein the first and second treatment members receive electrosurgical energy at a first potential and the third treatment member receives electrosurgical energy at a second potential different than the first potential such that tissue positioned between the first treatment member and the second treatment member is cut using bipolar electrosurgical energy.

4. The surgical instrument of claim 1, wherein the switch is configured to select a monopolar sealing mode wherein at least one of the first treatment member or the second treatment member receives electrosurgical energy at a first potential and electrically cooperates with a remotely disposed return pad such that tissue positioned between the first and second treatment members is sealed using monopolar electrosurgical energy.

5. The surgical instrument of claim 1, wherein the switch is configured to select a monopolar cutting mode wherein the third treatment member receives electrosurgical energy at a first potential and electrically cooperates with a remotely disposed return pad such that tissue positioned between the first treatment member and the third treatment member is cut using monopolar electrosurgical energy.

6. The surgical instrument of claim 1, wherein the switch is configured to select between at least two of bipolar sealing between the first and second treatment members, monopolar sealing between one of the first treatment member or the second treatment member and a remotely disposed return pad, bipolar cutting between the third treatment member and the first and second treatment members, and monopolar cutting between the third treatment member and the remotely disposed return pad.

7. The surgical instrument of claim 1, wherein the end effector includes a knife, and wherein at least one of the first and second treatment members includes a knife channel configured to facilitate reciprocation of the knife therethrough.

8. The surgical instrument of claim 1, further comprising an actuating rod extending through an actuation rod channel defined in the first treatment member, the actuating rod operably coupling the second actuator to the third treatment member of the second actuating device.

9. The surgical instrument of claim 8, wherein distal movement of the second actuator relative translates the actuating rod distally through the actuation rod channel such that the third treatment member is moved towards an open position relative to the first treatment member, and wherein proximal movement of the second actuator translates the actuating rod proximally through the actuation rod channel such that the third treatment member is moved towards a closed position relative to the first treatment member.

10. The surgical instrument of claim 9, wherein the first treatment member includes a first cutting edge and the third treatment member includes a second cutting edge, wherein the first and second cutting edges maintain contact while the third treatment member is moved between the open position and the closed position relative to the first treatment member.

11. The surgical instrument of claim 1, wherein the third treatment member includes a hooked portion configured for hooking tissue.

12. The surgical instrument of claim 1, wherein the first actuating device includes a first radius of curvature and the second actuating device includes a second radius of curvature that is greater than the first radius of curvature.

13. The surgical instrument of claim 1, wherein the first treatment member includes a first thickness and a downward sloping upper surface, and wherein the third treatment member includes a second thickness that is greater than the first thickness.

14. The surgical instrument of claim 1, wherein a distal end portion of the first treatment member and a distal end portion of the third treatment member extend beyond a distal end portion of the second treatment member such that a first thickness of the end effector at a distal end portion thereof is less than a second thickness of the end effector at a proximal end portion thereof.

15. The surgical instrument of claim 1, wherein the first treatment member includes a perimeter, and wherein the third treatment member is U-shaped and is disposed to surround the perimeter.

* * * * *